United States Patent [19]
Dale et al.

[11] Patent Number: 6,015,886
[45] Date of Patent: Jan. 18, 2000

[54] OLIGONUCLEOTIDE PHOSPHATE ESTERS

[75] Inventors: Roderic M. K. Dale, Wilsonville, Oreg.; Amy Arrow, Newtown, Conn.; Suresh C. Srivastava, Burlington; Syed K. Raza, Waltham, both of Mass.

[73] Assignees: ChemGenes Corporation, Ashland, Mass.; Oligos Etc., Inc., Wilsonville, Oreg.

[21] Appl. No.: 08/795,926

[22] Filed: Feb. 5, 1997

Related U.S. Application Data

[63] Continuation-in-part of application No. 08/662,447, Jun. 10, 1996, abandoned, which is a continuation of application No. 08/065,016, May 24, 1993, Pat. No. 5,525,719.

[51] Int. Cl.⁷ .......................... C07H 21/00; C07H 21/02; C07H 21/04
[52] U.S. Cl. .................. 536/23.1; 536/24.3; 536/24.5; 536/25.1; 435/6
[58] Field of Search ................................. 536/23.1, 25.1, 536/24.3, 24.5; 514/44; 435/6

[56] References Cited

U.S. PATENT DOCUMENTS

| | | | |
|---|---|---|---|
| 5,214,135 | 5/1993 | Srivastava et al. | 536/26.7 |
| 5,525,719 | 6/1996 | Srivastava et al. | 536/26.7 |
| 5,750,669 | 5/1998 | Rosch et al. | 536/24.3 |

FOREIGN PATENT DOCUMENTS

| | | |
|---|---|---|
| 0260032 | 3/1988 | European Pat. Off. . |
| 0339842 | 11/1989 | European Pat. Off. . |
| 4110085 | 10/1992 | Germany . |
| 2264792 | 4/1989 | Japan . |
| 9106309 | 5/1991 | WIPO . |
| 9415619 | 7/1994 | WIPO . |

OTHER PUBLICATIONS

Hirao et al., "Synthesis and Properties of an Initiation Codon Analog Consisting of 2'–O–methyl Nucleosides," Nucleosides Nucleotides, 9(8), 1113–1122 (1990); Chem. Abstr., 114(21), p. 873, Abstr. No. 207676t (May 27, 1991).

Kierzek et al.(I), "Some Steric Aspects of Synthesis of Oligoribonucleotides by Phosphoamidite Approach on Solid Support," Bull. Pol. Acad. Sci., Chem., 35(11–12), 507–516 (1988); Chem. Abstr., 110(7), p. 126, Abstr. No. 57990s (Feb. 13, 1989); both Abstract and original publication supplied.

Leonard et al., "A Convenient Preparation of Protected 2'–O–Methylguanosine," Nucleosides Nucleotides, 11(6), 1201–1204 (1992); Chem. Abstr., 117(17), p. 895, Abstr. No. 171915r (Oct. 26, 1992).

Yamana et al., "Synthesis and Properties of Oligonucleotides Bearing a Pendant Pyrene Group," in the Thirteenth Symposium on Nucleic Acids Chemistry, Nucleic Acids Symposium Series, No. 16, IRL Press, Osaka, Japan, Nov. 6–8,.1985, pp. 169–172.

Wagner et al., "A Simple Procedure for the Preparation of Protected 2'–O–Methyl or 2'–O–Ethyl Ribonucleoside–3'–O–phosphoramidites," Nucleic Acids Res., 19(21), 5965–5971 (1991).

Venijaminova et al., "Oligo(2'–O–Methylribonucleotides) and Their Derivatives. I. Automatic H–Phosphonate Synthesis of the Oligo(2'–O–Methylribonucleotides) Via H–Phosphonates," Bioorg. Khim., 16(5), 635–642 (Aug. 4, 1989); English abstract, Russian text.

Inoue et al.(I), "Synthesis and Hybridization Studies on Two Complementary Nona(2'–O–Methyl)ribonucleotides," Nucleic Acids Res., 15(15), 6131–6148 (1987).

Shibahara et al.(II), "Site–directed Cleavage of RNA," Nucleic Acids Res., 15(11), 4403–4415 (1987).

Alexandrova et al.(I), "Synthesis of Cytidylyl–(3'–5')–2'–O(and 3'–O)–Methyladenosine 3'–O (and 2'–O)–N–Formyl–L–methionyl Derivatives," Coll. Czech. Chem. Comm., 42, 1694–1704 (1977).

Alexandrova et al.(II), "Synthesis of Cytidylyl–(3'–5')–Cytidylyl–(3'–5')Adenosine Derivatives," Coll. Czech. Chem. Comm., 42, 1686–1693 (1977).

Gladkaya et al., "Synthesis of N,O–Protected Derivatives of 2'–O–Methylcytidine and 2'–O–Methyl– and N¹–Methylguanosines," Khim. Prir. Soedin., 1989(4), 568–573; Chem. Abstr., 112(21), p. 772, Abstr. No. 198947m (May 21, 1990).

Ishido et al., "Process for Synthesizing Oligonucleotides in a Homogeneous System Using Polysaccharide Derivatives as High Molecular Weight Protective Groups," PCT WO 88 03,149, published May 5, 1988; Chem. Abstr., 109(25), p. 910, Abstr. No. 231471q (Dec. 19, 1988); only abstract provided.

Rozners et al., "Synthesis of Oligoribonucleotides by the H–Phosphonate Method Using Base–Labile 2'–O–Protecting Groups. II. Some Aspects of Use of 2'–O–benzoyl and Anisoyl Protecting Groups," Bioorg. Khim., 16(11), 1531–1536 (1990).

Cotten et al., "2'–O–Methyl, 2'–O–Ethyl Oligoribonucleotides and Phosphorothioate Oligoribonucleotides as Inhibitors of the in vitro U7 snRNP–Dependent mRNA Processing Event," Nucleic Acids Res., 19(10), 2629–2635 (1991).

(List continued on next page.)

*Primary Examiner*—L. Eric Crane
*Attorney, Agent, or Firm*—Bozicrvic, Field & Francis, LLP; Diana L. DeVore

[57] ABSTRACT

This invention relates to synthetic oligonucleotides that are useful for antisense based therapeutic applications. The synthetic oligonucleotides of this invention have modifications in the sugar phosphate backbone for improved antisense properties.

14 Claims, 13 Drawing Sheets

OTHER PUBLICATIONS

Caruthers et al., "Synthesis of Oligonucleotides Using the Phosphoramidite Method," in Biophosphates and Their Analogues—Synthesis, Structure, Metabolism and Activity, report of the Proceedings of the 2nd International Symposium on Phosphorus Chemistry Directed Towards Biology, Bruzik & Stec [Eds.], Lodz, Poland, Sep. 8–12, 1986, Elsevier Science Publishers, Amsterdam, The Netherlands, pp. 3–21.

Kierzek et al.(II), "Synthesis of 2'–5'–Oligoribonucleotides on Solid Support by Phosphoramidite Method," Biophosphates and Their Analogues—Synthesis, Structure, Metabolism and Activity, report of the Proceedings of the 2nd International Symposium on Phosphorus Chemistry Directed Towards Biology, Bruzik & Stec [Eds.], Lodz, Poland, Sep. 8–12, 1986, Elsevier Science Publishers, Amsterdam, The Netherlands, pp. 179–184.

Robins et al., "Nucleic Acid Related Compounds. 12. The Facile and High–Yield Stannous Chloride Catalyzed Monomethylation of the Cis–Glycol System of Nucleosides by Diazomethane," *J. Org. Chem.*, 39(13), 1891–1899 (1974).

Heikkila et al., "5'–O–Trityl Groups Promoted Directive Effect in the Preparation of 2'–O–Methylribonucleosides," *Acta Chemica Scand.*, B36(10), 715–717 (1982).

Vaghefi et al., "A Convenient High Yield Synthesis of $N^4$–Isobutyryl–2'–O–methylcytidine and its Monomer Units for Incorporation into Oligonucleotides," Nucleosides Nucleotides, 12(10), 1007–1013 (1993); *Chem. Abstr.*, 121(1), p. 1049, Abstr. No. 9898y (Jul. 4, 1994); only Abstract provided.

Inoue et al. (II), "Sequence–dependent Hydrolysis of RNA Using Modified Oligonucleotide Splints and RNase H," *FEBS Letters*, 215(2), 327–330 (May 1987).

Sproat et al., "New Synthetic Routes to Protected Purine 2'–O–Methylriboside–3'–O–phosphoramidites Using a Novel Alkylation Procedure," *Nucleic Acids Research*, 18(1), 41–49 (1990).

$NH_3$/Pyridine reaction on standard base protected p-ethoxy oligonucleotides (17-mer)
Series 1 = full length base deprotected p-ethoxy oligonucleotides
Series 2 = base and phosphate deprotected oligomer species

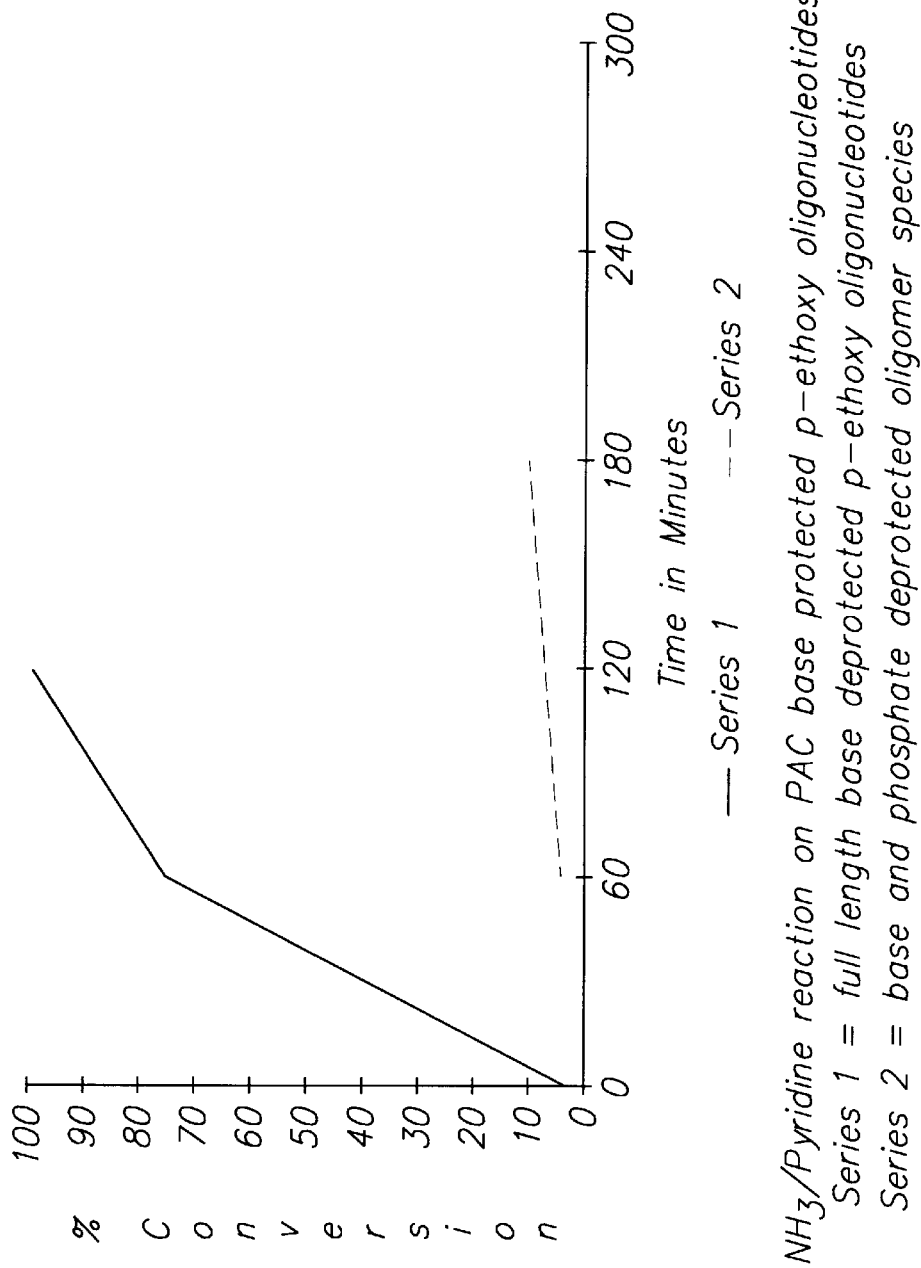

OLIGONUCLEOTIDE PHOSPHATE ESTERS

CROSS-REFERENCE TO RELATED APPLICATION

This application is a continuation-in-part application of U.S. application Ser. No. 08/662,447, filed Jun. 10, 1996, now abandoned, which is a continuation application of U.S. application Ser. No. 08/065,016, filed May 24, 1993, now U.S. Pat. No. 5,525,719.

FIELD OF THE INVENTION

This invention relates to synthetic oligonucleotides that are useful for antisense based therapeutic applications. The synthetic oligonucleotides of this invention have modifications in the sugar phosphate backbone for improved antisense properties.

BACKGROUND OF THE INVENTION

Antisense (i.e. sequences complementary to the "sense" strand, usually the messenger RNA) and otherwise interfering (e.g. "decoy") oligonucleotides, oligoribonucleotides, and modified oligonucleotides (collectively referred to herein as ASOs) are gaining overwhelming popularity for interference in various steps leading from DNA transcription to mRNA translation. This regulatory interference can be harnessed for therapeutic effects against many diseases and viral infections. Production of viral proteins can be inhibited by oligonucleotides that are complimentary to portions of mRNA for that protein (i.e. antisense). Other regulatory mechanisms of viruses, such as HIV, are also open to interference with the use of complimentary (i.e. antisense), or decoy (i.e. sense) oligonucleotides. Oligonucleotides for therapy have several advantages. These advantages include the extremely high specificity and the ease of design afforded by Watson-Crick base pairing. The high association constants imply a strong duplex formation and thus effectiveness at low concentrations.

An ideal therapeutic agent should be (a) specific for the target, (b) selective for the target (i.e. minimum nonspecific effects), (c) non-toxic to the host, with a large therapeutic window, (d) effective at low concentrations, and (e) effective at eliminating the pathogen, rather than merely reducing the pathogen level.

For ASO therapy, several criteria are important. (i) The ASOs must be stable to degradation in vivo. (ii) The ASOs must be efficiently taken up by the cells. (iii) The ASOs must be retained by the cells. (iv) The ASOs must effectively interact with the target. (v) The ASOs should not nonspecifically interact with other cellular factors. (vi) The cost of production should be low. (vii) The ASOs should have low toxicity, immunogenicity, mutagenicity, and should have a large therapeutic window. (viii) In addition, an ASO that allows RNaseH activity upon binding its target has a significant advantage as antisense to MnRNA, since the mRNA in the mRNA-ASO hybrid may be hydrolyzed by RNaseH, thereby destroying the mRNA, and releasing the ASO, thus creating a catalytic cycle. This is especially important in the case of many viral infections, such as HIV, since the reverse transcriptase; which is localized primarily in the cytoplasm itself, has RNaseH activity. Cellular RNaseH has been thought to be localized primarily in the nucleus, and to some extent in the cytoplasm as well. Natural phosphodiester ASOs are subject to nuclease activity and therefore possess a short half-life.

Natural oligonucleotides and their several modified analogs are widely used as tools for regulating specific gene expression (Wickstrom, E. L., Bacon, T. A., Gonzalez, A., Freeman, D. L., Lyman, G. H., Wickstrom, E., Proc, *Natl. Acad. Sci., USA,* 85, 1028–1032 (1988). They have been used for blocking, splicing and translation of mRNA (Blake, K. R., Murakami, A., Miller, P. S., *Biochemistry,* 24, 6132–6138 (1985); Haeuptle, M. T., Frank, R., Dobberstein, B., *Nucl. Acids Res.,* 14, 1427–1448 (1986); Gupta, K. C., *J. Biol. Chem,* 262, 7492–7496 (1987); Maher, L. J., Dolnick, B. J., *Nucl. Acids Res.,* 16, 3341–3358 (1988)). Originally the work of Zamecnik showed that a large excess of a natural antisense oligonucleotide can block the replication of Rous Sarcoma virus in chick fibroblast cells (Zameknik, P. C., and Stephenson, M. L., *Proc. Natl. Acad. Sci., USA,* 75, 285–288 (1978). This work was followed by other workers (Smith, C. C., Aurelain, L., Reddy, M. P., Miller, P. S., and Ts'O, P. O. P., *Proc. Natl. Acad. Sci., USA,* 83, 2787–2791 (1986); Zerial, A., Thoung, N. T., Helen, C., *Nucl. Acids Res.,* 15, 9909–9919 (1987). Natural phosphodiester deoxy and ribonucleotides suffer from the disadvantage of rapid degradation by intracellular enzymes. Antisense oligos fall into two basic categories with respect to charge, charged, and uncharged molecules. There are distinct advantages for both types of molecules depending upon the cell types desired and specific use.

RNaseH has been used for cleaving an RNA strand of RNA-DNA hybrid at several positions when preparing small fragments from the large RNA molecules (Stein, H., and Hausen, P., Science, 166, 393–395 (1969).; Hausen, P., and Stein, H., *Eur. J. Biochem.* 14, 278–283, (1970).; Henry, C. M., Ferdinand, F. J., and Knippers, R., *Biochem. Biophys. Res. Conl.,* 50, 603–611 (1973).; Donis-Keller, H., *Nucl. Acids Res.,* 7, 179–192 (1979).; Ruskin, B., Krainer, A. R., Maniatis, T., and Green, M. R., *Cell,* 38, 317–331 (1984).; Schmelzer, C. and Schweyen, R. J., *Cell,* 46, 557–565 (1986).)

Synthetic short DNA oligomers (tetramers to hexamers) complimentary to a specific site in the RNA molecule, have been employed from the method of Donis-Keller, ibid. Using complimentary chimeric (hybrid) oligonucleotides containing deoxyoligonucleotides and 2'-O-methylribonucleotides, a site directed cleavage of enzymatically synthesized 90-mer RNA at a single site was achieved with *E. coli* RNaseH (Shibahara, S., Muhai, S., Nishihara, T., Inoue, H., Ohtsuka, E., Morisawa, H., *Nucl. Acids Res.,* 15, 4403–4415 (1987)). At the same time it should be noted that 2'-O-methylribonucleotides containing RNA-RNA duplex is not a substrate for RNaseH. 2'-O-methylriboligonucleotides have been used in the purification of RNA-protein complexes from crude nuclear extracts (Blencowe, B. J., Sproat, B. S., Barbino, S., and Lamond, A. I., *Cell,* 59, 531–539 (1989). and Barbin, S., Sproat, B. S., Ryder, U., Blencowe, B. J., and Lamond, A. I., *EMBO Journal,* 8, 4171–4178 (1989)). The presence of 2'-O-methylribonucleotides in an RNA confers protection against nuclease digestion and are completely resistant to degradation by either RNA or DNA specific nucleases (Sproat, B. S., Lamond, A. I., Beijer, B., Neuner, P., and Ryder, U., *Nucl. Acids Res.,* 17, 9, 3373 (1989)) and against alkaline hydrolysis. Similarly, it has also been demonstrated that a 2'-O-methyloligoribonucleotide-RNA duplex is much more thermally stable than the corresponding oligodeoxynucleotide-RNA duplex (Inoue, H., Imura, A., Iwai, S., Miura, M., Ohtsuka, E., *Nucl. Acids Res.,* 15, 6131–6148 (1989)). Furthermore, as pointed out above, the former duplex is not a substrate for RNaseH (Inoue, H., Hayase, Y., Iwai, S., Ohtsuka, E., *FEBS Letters,* 215, 327–330 (1987)).

Phosphorothioate oligonucleotides are another modification of natural oligodeoxy and oligoribonucleotides which were shown to possess antiviral activity (Matsukura, M., Shinozuka, K., Zon, G., Mitsuya, H.; Reitz, M., Cohen, J. S., Broder, S., *Proc. Natl. Acad. Sci., USA*, 84, 7706–7710 (1987)); (Matsukura, M., Shinozuka, K., Zon, G., Mitsuya, H., Wong-Staal, F., and Cohen, J. S., *Clinical Res.*, 36, 463A (1988)). It has been demonstrated that phosphorothioate DNA can function by activating endogenous RNaseH that will cleave the targeted RNA (Agarwal, S., Maynard, S. H., Zamecnik, P. C., Paderson, T., *Proc. Natl. Acad. Sci., USA*, 87, 1401–1405 (1990); Woolf, T. M., Jennings, C. G., Rebagliati, M., and Melton, D. A., *Nucl. Acids Res.*, 18, 1763–1769 (1990)). With the notable exception of phosphorothioate DNA, the vast majority of nuclease resistant modified DNA backbone are not recognized by RNaseH. While phosphorothioate DNA has the advantage of activating RNaseH, it has the disadvantage of non-specific effects and reduced affinity for RNA. (Stein, C. A., Matsukara, M., Subasinghe,. C., Broder, S., Cohen, J. S., *Aids Res. Hum. Retroviruses*, 5, 639–646 (1989); Woolf, T. M., et al, ibid). Chimeric (also called gapmer) antisense oligos that have a short stretch of 6–9 nucleotides have been used to obtain RNaseH mediated cleavage of the target RNA, while reducing the number of phosphorothioate linkages (Dagle, J. M., Walder, J. A., Weeks, D. L., *Nucl. Acids Res.*, 18, 4751–4757 (1990); Agarwal, S., Maynard, S. H., Zamecnik, P. C., Paderson, T., *Proc. Natl. Acad. Sci., USA*, 87, 1401–1405 (1990)). The chimeric oligonucleotides (gapmers or hybrids) have been designed in the past to have a central region that forms a substrate for RNaseH that is flanked by hybridizing "arms", comprised of modified nucleotides that do not form substrate for RNaseH. In these chimeras (gapmers or hybrids), the substrate for RNaseH that forms the "gap" can be on the 5'- or 3'-side of the oligomer.

The "arm" which does not form a substrate for RNaseH has the following relevant properties. They hybridize to the target providing the necessary duplex affinity to achieve antisense inhibition. They reduce the number of phosphorothioate DNA linkages in the oligomer, thus reducing non-specific effects. Lastly, they limit the region that forms a substrate for RNaseH, thus adding to the target specificity of the oligomers. Several chemistries have been used to make the regions of a chimeric oligomer that are not a substrate for RNaseH. The first chimeric oligomers used methyl phosphonate or phosphoramidate linkages in the arms ((Dagle, J. M., Walder, J. A., Weeks, D. L., *Nucl. Acids Res.*, 18, 4751–4757 (1990); Agarwal, S., Maynard, S. H., Zamecnik, P. C., Paderson, T., *Proc. Natl. Acad. Sci., USA*, 87, 1401–1405 (1990)).

While these compounds functioned well in buffer systems and Xenopus oocytes, the "arm" decreased the hybrid affinity. This decrease in affinity dramatically reduced the activity of oligomers in mammalian culture.

Methyl phosphonate modified oligodeoxy and ribonucleotides have been employed as antisense in the past. The replacement of an oxygen by a methyl group in methyl phosphonate oligodeoxynucleotides disturbs the conformation around the P-O3 and P-O5 linkages, due to stereoelectronic factors. Therefore, longer (>8 nucleotides) methyl phosphonate systems do not readily adopt a helical geometry, resulting in poor hybridization with natural DNA. Indeed, it has been found that methyl phosphonate. 21-niers have a low antisense activity, compared to shorter oligos (Marcus-Sekura, C. J., *Anal. Biochem.*, 172, 289–295 (1988). Many oligos containing methyl phosphonate backbone oligodeoxyribonucleoside methylphosphonates of defined sequence were prepared and extensively characterized (Miller, P. S., Reddy, P. M., Murakami, A., Blake, K. R., Lin, S. B., Agris, C., *Biochemistry*, 25, 5092 (1986)). They were shown to be resistant to several exonucleases (Agarwal, S., Goodchild, J., *Tet. Lett.*, 28, 3539 (1987)). The methyl phosphonates were shown to hybridize with mRNA in Agarose gel (Murakami, A., Blake, K. R., Miller, P. S., *Biochemistry*, 24, 4041 (1985)).

Methylphosphonate oligodeoxynucleotides (MP), complementary to specific regions of the bcr-abl mRNA of Philadelphia chromosome, present in chronic myelogenous leukemia (CML) condition, were incorporated in liposomes. The liposomal MP (L-MP) caused inhibition of the growth of CML cells (Tari, A. M., Tucker, S. D. T., Deisseroth, A., Berestein, G. L., *Blood*, 84, 601–607 (1994).

Phosphoramidates, such as N-methoxyphosphoramidate oligonucleotides, have been synthesized. However, they form less stable duplexes with complimentary sequences, when compared to "all diester" oligomers. The analog, however, was found to be highly resistant to nucleases (Peyrottes, S., Vasseur, J. J., Imbach, J. L., Rayner, B., *Nucleosides and Nucleotides*, 13, 2135–3149 (1994)). Other reports have shown high stability to enzymatic cleavage but lower binding affinity for the DNA and RNA targets (Froehler, B. C., *Tet. Lett.*, 27, 5575 (1986); Froehler, B. C., Matteucci, M. D., *Nucl. Acids. Res.*, 16, 4831 (1988); Jager, A., Levy, M. J., Hecht, S. M., *Biochemistry*, 27, 7237 (1988); Letsinger, R. L., Singman, C. N., Histand, G., Salunkhe, M., *J. Am. Chem. Soc.*, 110, 4470 (1988); Agarwal, S., Goodchild, J., Civeria, M. P., Thornton, A. H., Sarin, P. S., Zamecnik, P. C., *Proc. Natl. Acad. Sci., USA*, 85, 7079, (1988)). These modifications are not able to direct RNaseH cleavage.

A number of studies have been reported for the synthesis of phosphate alkylated (methyl and ethyl phosphotriester) oligonucleotides and their physico-chemical and biochemical evaluation. Dinucleotides with methyl and ethyl triesters were shown to possess greater affinity towards polynucleotides possessing complementary sequences (Miller, P. S., Fang, K. N., Kondo, N. S., Ts'O, P. O. P., *J. Am Chem. Soc.*, 93, 6657, (1971)). However, a few years ago, another group reported lack of, or poor binding affinity of, heptethyl ester of oligothymidine with complementary polynucleotides (Pless, R. C., and Ts'O, P. O. P., *Biochemistry*, 16, 1239–1250 (1977)). Phosphate methylated oligonucleotides were synthesized and found to possess resistance towards endonuclease digestion (Gallo, K. L., Shao, K. L., Phillips, L. R., Regan, J. B., Kozioikiewicz, Uznanski, B., Stec, W., Zon, G., *Nucl. Acids Res.*, 18, 7405 (1986)). A phosphate methylated 18-mer oligonucleotide was shown to have high Tm value in duplexes with natural DNA and blocked the DNA replication process at room temperature (Moody, H. M., van Genderen, M. H. P., Koole, L. H., Kocken, H. J. M., Meijer, E. M., Buck, H. M., *Nucl. Acids Res.*, 17, 4769–4782 (1989)). These authors postulated that phosphate ethylated oligonucleotides would have poor antisense properties. Phosphate methylated dimers of DNA bases were synthesized using transient protecting group of FMOC for the exocyclic amino groups (Koole, L. H., Moody, H. M., Broeders, N. L. H. L., Quaedflieg, P. L. L. M., Kuijpers, W. H. L., van Genderen, M. H. P., Coenen, A. J. J. M., vanderWal, S., Buck, H. M., *J. Org. Chem*, 54, 1657–1664 (1989)).

Synthesis and physico-chemical properties of partial methylated oligodeoxyribonucleotides were determined. Only the thymidine and cytidine oligomers with methyl phosphotriester could be prepared satisfactorily due to difficulty in maintaining methyl triester intact. Furthermore, the methyl group was found to have a destabilizing effect on the hybridization properties of the modified oligomers with its complementary sequence by comparison with the unmodified parent oligodeoxynucleotide (Vinogradeov, S., Asseline, U., Thoung, N. T., *Tet. Lett.,* 34, 5899–5902 (1993)).

Few other reports have postulated that phosphate methylated oligonucleotides are preferable as antisense DNA based on stronger hybridization than methyl phosphonate or phosphate ethylated systems (van Genderen, M. H. P., Koole, L. H., Merck, K. B., Meijer, E. M., Sluyterman, L. A. A. E., Buck, H. M., *Proc. Kon. Ned Akad. van Wetensch.,* B90,155–159 (1987); van Genderen, M. H. P., Koole, L. H., Buck, H. M., *Recl. Trav. Chim. Pays Bas,* 108, 28–35 (1989)). The later authors carried out certain protein binding studies with p-methoxy and p-ethoxy oligonucleotides and postulated on the hypothesis of protein induced DNA duplex destabilization by such oligonucleotides.

Phosphate ethylated systems were shown by the same authors to display comparatively poor hybridizing properties, and postulated to have poor antisense properties (Moody, H. M., van Genderen, M. H. P., Koole, L. H., Kocken, H. J. M., Meijer, E. M., Buck, H. M., *Nucl. Acids Res.,* 17, 4769–4782 (1989)). p-isopropoxyphosphoramidites containing p-O-methyl have been synthesized from several nucleosides (Stec, W. J., Zon, G., Gallo, K. A., Byrd, R. A., *Tet. Lett.,* 26, 2191–2194 (1985)), and a few short oligonucleotides were synthesized, and hybridization studies were carried out. A few short oligonucleotides containing p-O-methyl were synthesized using 2-(acetoxymethyl) benzoyl (AMB) as a nucleoside base protecting group. (Kuijpers, W. H. A., Huskens, J., van Boeckel, C. A. A., *Tet. Lett.,* 31, 6729–6732 (1990)). However, no biological activity or related properties were reported. These authors have further reported the application of AMB protecting group to synthesize methyl phosphonate containing oligodeoxynucleotides (Kuijpers, W. H. A., Yeheskiely, E. K., van Boom, L. H., van Boeckel, C. A. A., *Nucl. Acid Res.,* 21, 3493–3500 (1993)).

SUMMARY OF THE INVENTION

The inventors have discovered that oligonucleotides containing p-ethoxy backbones, as well as chimeric or gapmer oligonucleotides using p-ethoxy oligodeoxynucleotides, p-ethoxy-2'-O-methyl oligonucleotides and chimeras containing these critical backbones, by way of illustration, fulfills the criteria for an ideal therapeutic agents. In addition, these oligonucleotides represent a significant improvement over the only other neutrally charged backbones-methyl phosphonate backbones. The oligodeoxynucleotide and 2'-O-methyloligonucleotides of the present discovery contain p-ethoxy backbone and show nuclease resistance, and Tm values that are superior to that of phosphorothioates. The p-ethoxy oligodeoxy nucleotides and the 2'-O-methyl-p-ethoxy oligonucleotides of the inventors' discovery further show ability to activate bacterial RNaseH as well as significant specific gene inhibition in antisense assays.

In an earlier patent application by Monia (WO 94/08003), oligomers are described that have 2'-O-methyl hybridizing "arms" without phosphorothioates in the "arms". While Monia shows that these oligomers may function in some cases., the inventors herein found that the oligomers with a long 2'-O-methyl "arms" have reduced activity compared to the 2'-O-methyl phosphdrothioate "arms" (see FIG. 14). This may be due to exonucleases degradation of the 2'-O-methyl phosphodiester linkages.

The present invention shows that a 25-mer oligonucleotide containing 9 phosphorothioate linkages at the 5'-terminus, followed by sixteen-p-ethoxy-2'-O-methyl linkages has specific antisense activity in cell culture. Additionally the present invention shows that p-ethoxy oligonucleotide, p-ethoxy2'-O-methyl oligonucleotides, as well as chimeras of these backbones containing a phosphorothioate DNA gap in middle, inhibits the targeted gene by antisense mechanisms.

This invention describes the use of synthetic p-alkoxy deoxyoligonucleotides and 2'-O-methyl-p-alkoxy oligonucleotides (called herein collectively as PA-oligonucleotides) which have nonionic internucleotide linkages, as well as chimeras containing these linkages along with phosphorothioate. They exhibit useful antisense properties. The oligonucleotide analogs of this invention are highly nuclease resistant, form a very stable duplex with RNA, and have a strong hydrophobicity for efficient cellular uptake. The oligonucleotides of this invention have been found to possess bacterial RNaseH activity. The illustration of the RNaseH activity, by way of example, has been demonstrated for *E. coli* RNaseH. The discovery of this biological property in the PA-oligonucleotides of this invention, combined with enhanced affinity for the complementary oligomer and the other associated properties, as well as the combination of these unique properties as outlined, demonstrates that these oligonucleotides offer significant advantages as a class of compounds for the development of therapeutics that had not been previously observed. The term oligonucleotide refers to both 2'-deoxy oligonucleotide and ribooligonucleotides. The minimum requirement is one phosphate alkyl ester. The oligonucleotide consists of polymers of one or more nucleotide monomers, 2'-deoxy or ribonucleotides, connected together or linked to a monomer by at least one 5'- to 3'-internucleotide linkages. These linkages include any of the linkages known in the antisense oligonucleotide art. Thus they could be, but are not limited to, 2'-5'-polyadenosine (2'-5'-A-(A)nA), at the 5'-end, 3'-end or in between an oligonucleotide sequence. Similarly the linkage could be 3'-T-3'-oligonucleotide linkage (inverted T) at the 3'-end of an oligonucleotide, in between the oligonucleotide sequence, or at the 5'-end of an oligonucleotide. In addition, the term oligonucleotide includes molecules besides the natural pyrimidine and purine bases, adenine, cytosine, thymine, inosine, also having modified nucleic acids bases. It is intended that the present invention cover both natural and modified nucleobases including radicals such as 9-adeninyl, 1-thyminyl, 1-cytosinyl, 9-guaninyl, 9-hypoxanthinyl, 1-(5-methylcytosinyl), 1-(5-azacytosinyl), 1-(5-bromouracilyl), 1-(5-bromocytosinyl), 1-(5-fluorouracilyl), 1-(5-fluorocytosinyl), 1-(5-chlorocytosinyl ), 1-(5-chlorouracilyl), 1-(5-iodouracilyl), 1-(5-iodocytosinyl), 1-1(5-propynyluracilyl) and 1-(5-propynylcytosinyl). The term oligonucleotide also includes, but is not limited, to natural deoxyribose and ribose sugar, and modified sugar with substitutions, such as 2'-halo groups, such as fluoro, chloro, bromo, iodo and 2'-amino lipophilic groups, such as cholesterol. The other 2'-group of the ribose moiety of nucleoside units include, but are not limited to 2'-O-methyl, 2'-O-ethyl, 2'-O-propyl, their higher homologs, and isoforms, 2'-O-allyl, substituted alkoxy, acyl, acloxy, carboxy, trifluoro methyl, and carbalakoxy groups. The oligonucleotide analogs of this invention range from about 2 to about 60 nucleotide units in length, and most preferably about 20 nucleotide in chain length.

Thus, oligonucleotides of this invention will have from 1 to 59 phosphate esters, preferably comprising 50% or more of the internucleosidyl linkages along with a combination of phosphate linkages consisting of, but not limited to, phosphodiester, phosphorothioate, phosphoramidites, alkylphosphonates, phosphorocarbamates, and phosphorocarbonates. Theses are considered chimeric or hybrid oligonucleotides. This invention also provides therapeutic guidelines for treatment of viral infections, infections of pathogenic organisms, diseases resulting from abnormal gene expression or expression of an abnormal gene product. The pharmaceutical formulation could constitute a physiological acceptable carrier, such as lipofectin. This invention also provides guidelines for inhibiting the expression of gene function of a viral gene, a gene of a pathogenic organism, or a cellular gene using the oligonucleotide analogs described herein. Furthermore, the oligonucleotides of this invention provide a method of treating a mammal infected with a virus or pathogenic organism, disease or disorder, targeting abnormal gene product. The method includes administering therapeutic pharmaceutical formulations including the oligonucleotides of this invention. The dosage amount would be dependent on the stability of the duplex derived from the target nucleic acid, or the messenger RNA of the virus, pathogen and, thereby, inactivating it. The pharmaceutical formulation can be administered by one of several routes for such drug delivery, including oral, intranasal, intravenous, topical, rectal administration. The oligonucleotides of this discovery can be used in combination therapy along with other compatible drugs.

BRIEF DESCRIPTION OF THE FIGURES

FIG. 16 shows a graph of NH3/Pyridine reaction on PAC base protected p-ethoxy oligonucleotides (17 mer). Series 1 is the full length base deprotected p-ethoxy oligonucleotides. Series 2 is base and phosphate deprotected oligomer species.

DETAILED DESCRIPTION OF THE PREFERRED EMBODIMENTS

The present invention provides oligonucleotide analogs characterized by having at least one internucleotide phosphate bond modified as alkyl phosphotriester. The remaining linkages can be, but are not limited to, phosphorothioates, phosphorodithioates, alkyl phosphonates, or alkyl phosphorothionates, and morpholino oligomers. The modifications of the oligonucleotide sugar backbone in this invention have been shown to demonstrate resistance to nuclease mediated digestion of the therapeutic oligonucleotide. The number of alkyl phosphate ester linkages can range from one to as many internucleotide linkages that are present in the oligonucleotide. Thus for the purpose of the present invention, the term "oligonucleotide alkyl phosphotriester" is intended to encompass every such embodiment.

Digestion of full length modified (p-ethoxy and phosphorothioates), and unmodified oligonucleotides (phosphodiesters) was carried out by various nucleases. Model studies were also performed to determine the digestion of the various oligonucleotides of the present discovery with various exonuclease. There was observed a distinct slow breakdown of the p-ethoxy oligonucleotides of this discovery as compared to unmodified natural oligonucleotides (phosphodiester oligonucleotides). The digestion pattern was quite similar with the enzymes S1 nuclease, p1 nuclease, and Micrococcal nuclease. In a comparison study of p-ethoxy modified oligonucleotides and phosphorothioate modified oligonucleotides the rate of digestion was quite similar. (See Table 1, which shows the percent digestion of full length modified and unmodified oligonucleotides by various nucleases.

TABLE 1

| Oligo Type: | S1 Nuclease | PI Nuclease | Micrococcal Nuclease |
| --- | --- | --- | --- |
| O-Oligo 15 minutes | 99.70% | 29.80% | 95.00% |
| O-Oligo 30 minutes | 99.70% | 58.40% | 96.60% |
| S-Oligo 15 minutes | 17.00% | n/c | 2.50% |

TABLE 1-continued

| Oligo Type: | S1 Nuclease | PI Nuclease | Micrococcal Nuclease |
| --- | --- | --- | --- |
| S-Oligo 30 minutes ate,pH 7.2 | 18.50% | 3.30% | 3.00% |
| p-Ethoxy 15 minutes | 13.50% | 1.80% | 6.50% |
| p-Ethoxy 30 minutes | 23.50% | 6.40% | 19.30% |

RNaseH Activation Data

Figure 1A:
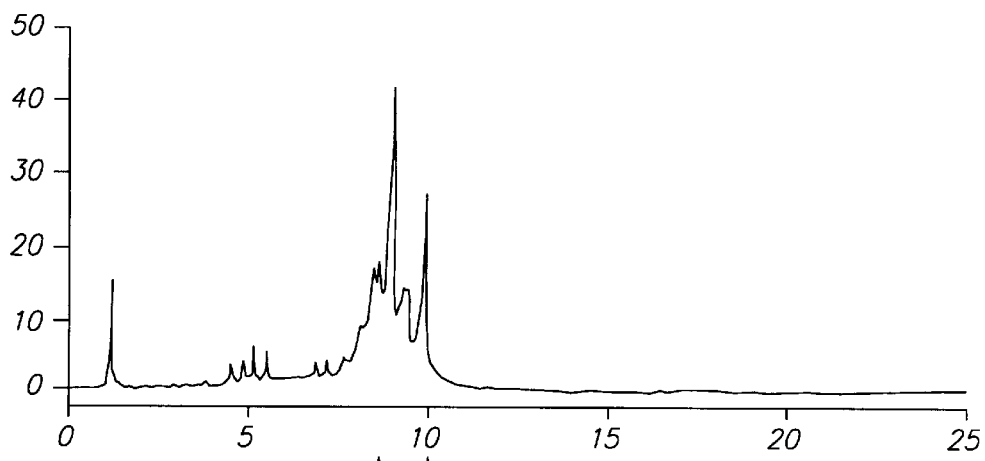
FIG. 1a is an HPLC graph of RvsA stock, (RNA114.27) sense strand annealed to ANT114.27 (O-oligo version of oligonucleotide (NBT114.27), peak at 8.8 minutes—ANT, peak at 9.8 minutes—RNA.
Figure 1B:
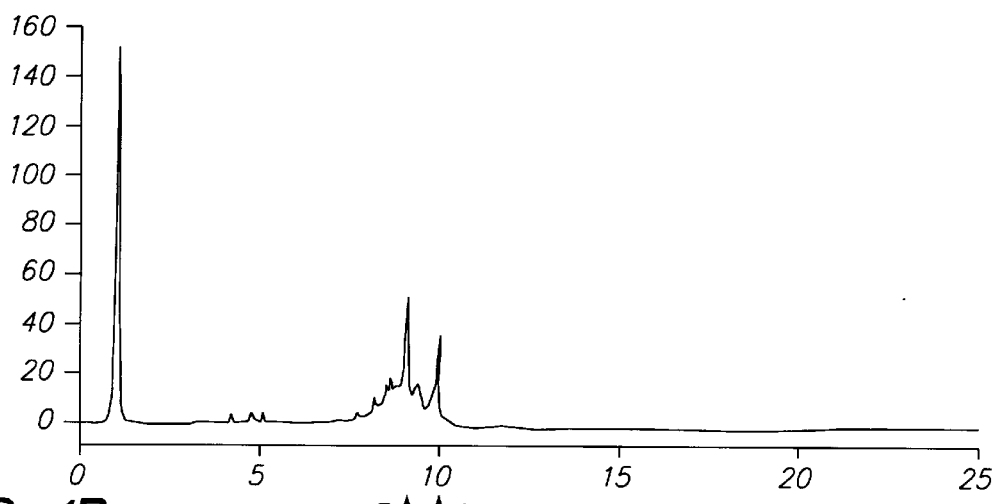
FIG. 1b is an HPLC graph of RvsA and RNaseH buffer, (RNA114.27) and (ANT114.27), duplex incubated in RNaseH buffer for 30 minutes, peak at 9.2 minutes—ANT, peak at 10.1 minutes—RNA. (Note: Time shift due to either load or different salt conditions).
Figure 1C:
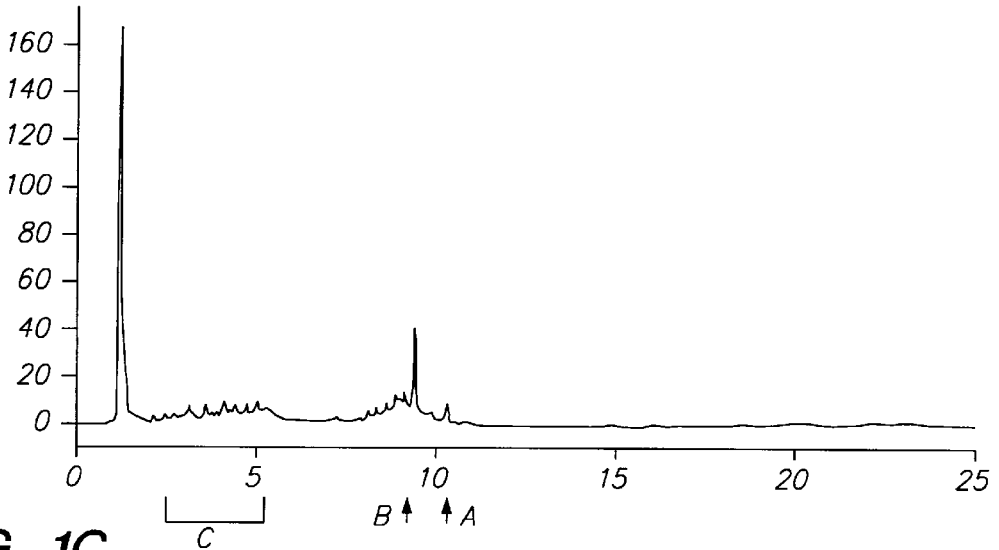
FIG. 1c is an HPLC graph of RvsA and RNaseH enzyme, (RNA114.27) and (ANT114.27), duplex incubated in RNaseH Buffer and RNaseH enzyme for 30 minutes. Peak at 9.3 minutes—ANT, peak at 10.2 minutes—RNA, severely reduced. RNaseH sensitive. Peaks at 2–6 minutes show a build up of short fragments.
Figure 1D:
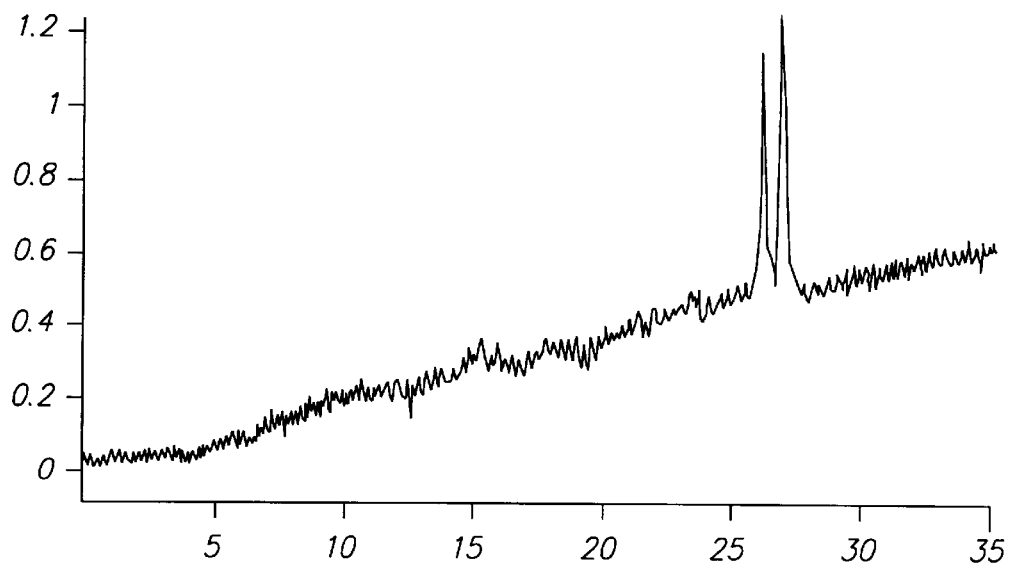
FIG. 1d is an HPLC graph of a repeat run on CE (capillary gel electrophoresis), with conditions the same as FIG. 1a. Both strands visible (load is low.) (RNA114.27) and (ANT114.27), peak at 25.5 minutes, and peak at 26.5 minutes, respectively.
Figure 1E:
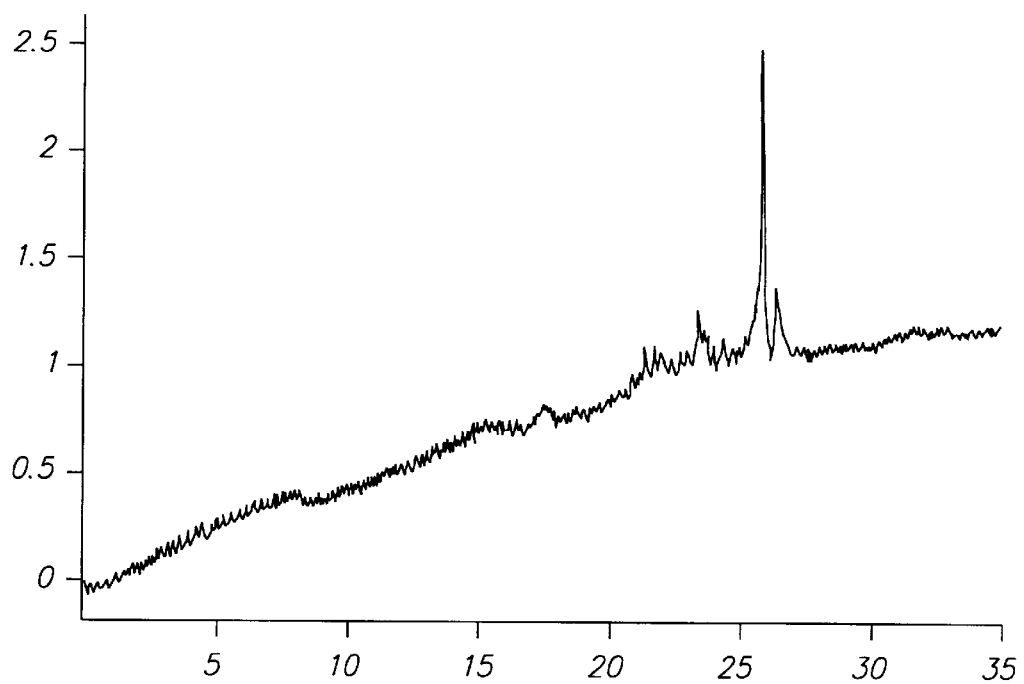
FIG. 1e is an HPLC graph of a repeat run on CE, with the same conditions as FIG. 1c, above. One peak severely reduced. (RNA114.27) and (ANT114.27), peak at 25.5 minutes, peak at 26.5 minutes-severely reduced, respectively. RNaseH sensitive.
Figure 2A:
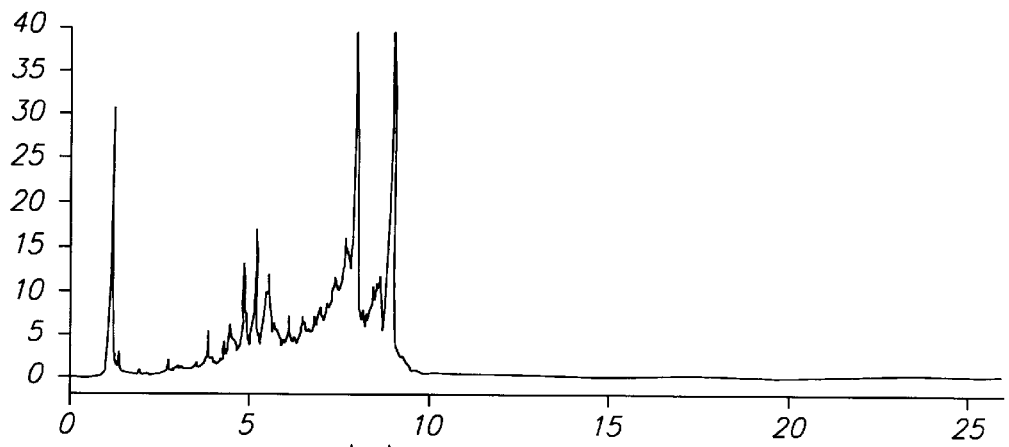
FIG. 2a is an HPLC graph of DvsA stock, (DNA114.27) sense strand annealed to ANT114.27, peak at 7.8 minutes—DNA; peak at 8.8 minutes—ANT, both DNA.
Figure 2B:
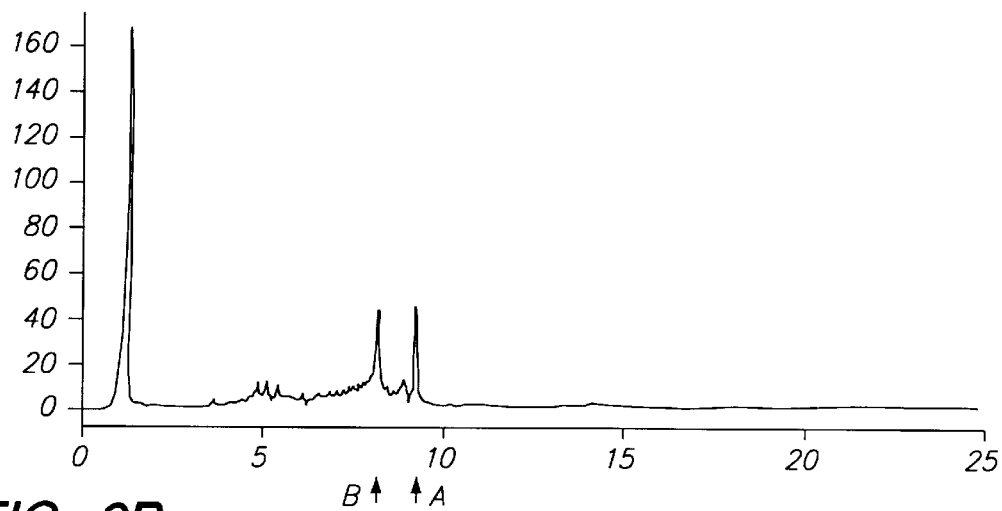
FIG. 2b is an HPLC graph of DvsA plus RNaseH= DNA114.27/ANT114.27 Duplex incubated in RNaseH buffer 30 minutes. Peak at 8.2 minutes is DNA, peak at 9.2' is ANT. (Note: Time shift due to either load or different salt conditions)
Figure 2C:
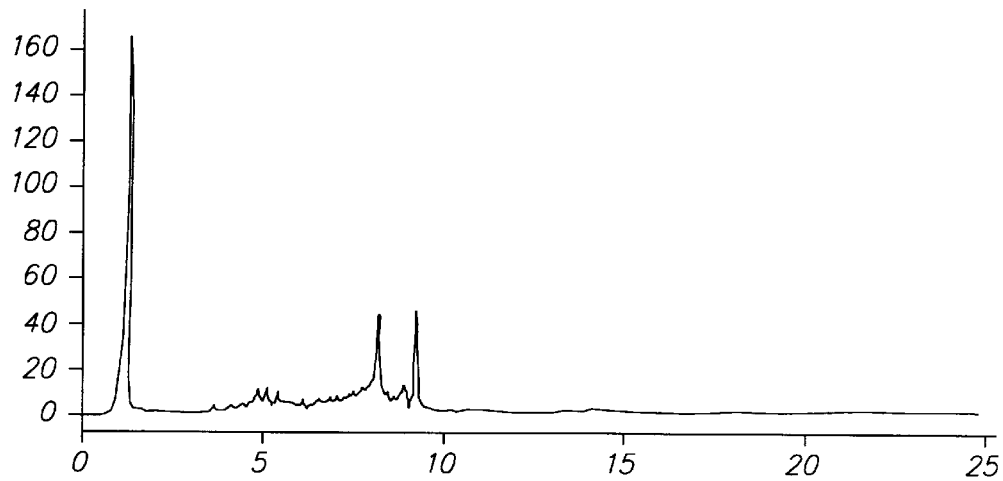
FIG. 2c is an HPLC graph of DvsA plus RNaseH, (DNA114.27) and. (ANT 114.27). Duplex incubated in RNaseH buffer, and RNaseH enzyme for 30 minutes. Peak at 8.2 minutes is DNA, peak at 9.3 minutes is ANT. (No effect of RNaseH compare to FIG. 1c).
Figure 3A:
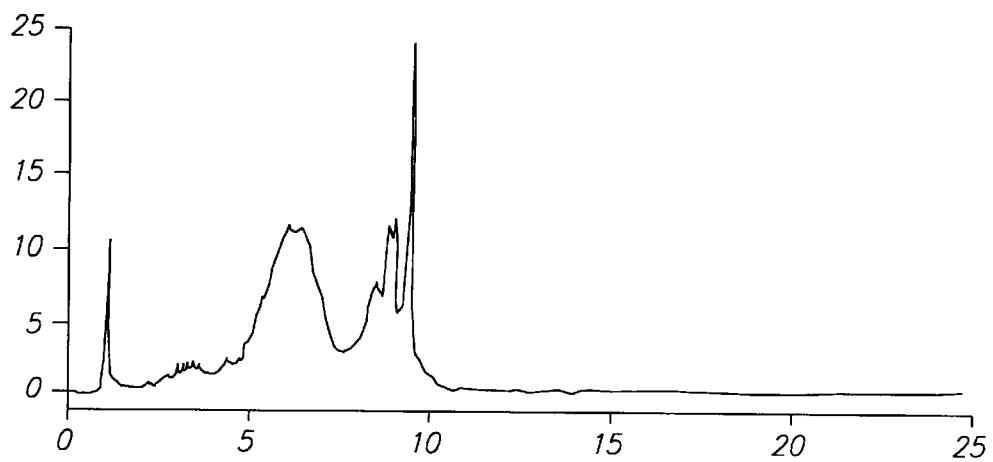
FIG. 3a is an HPLC graph of RNA vs. 9 stock, (RNA114.27) annealed to (p-thoxy/DNA99-9), chimeric, Peak at 9.4 minutes—RNA114.27, Peak at 5.7 minutes-p-ethoxy/DNA 999.
Figure 3B:
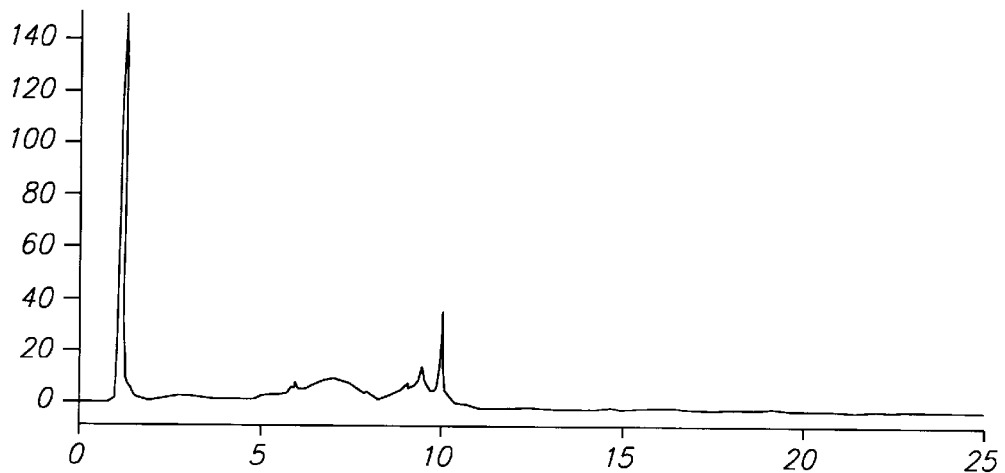
FIG. 3b is an HPLC graph of RNA vs. p-ethoxy DNA 999 and RNaseH buffer only, (RNA114.27) and p-ethoxy-DNA 999), duplex incubated in RNaseH buffer 30 minutes, peak at 6–8 minutes (p-ethoxy/DNA 999), peak at 10.1 minutes (RNA).
Figure 3C:
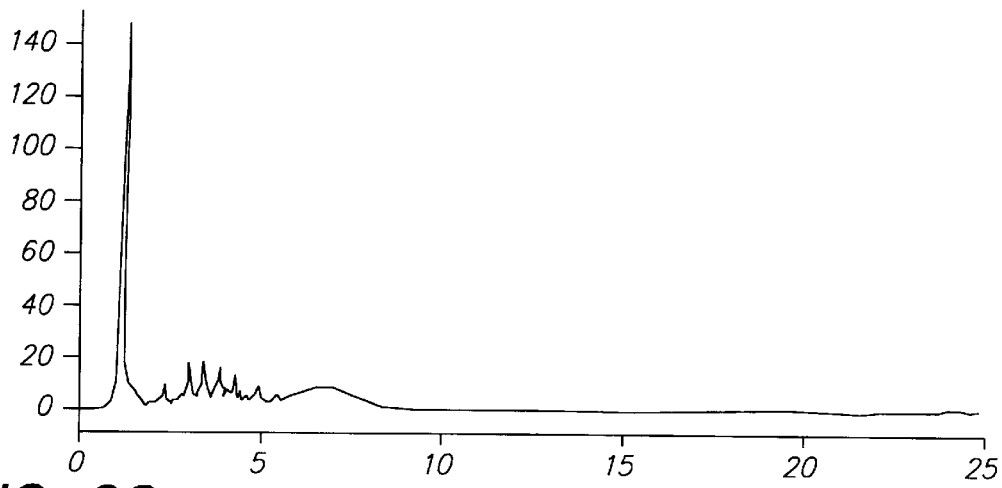
FIG. 3c is an HPLC graph of RNA vs. 999 and RNaseH enzyme, (RNA114.27) and (p-ethoxy-DNA 999), duplex incubated in RNaseH buffer and RNaseH 30 minutes, peak at 6–8 minutes (p-ethoxy DNA 999), peak at 2–5.5 minutes. (RNase sensitive, degradation fragments).
Figure 4A:
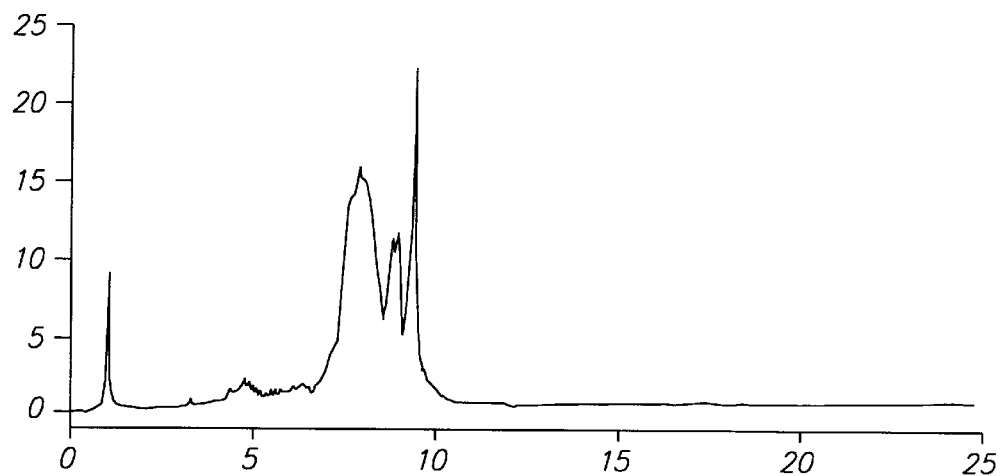
FIG. 4a is an HPLC graph of RNA vs. 21 p-ethoxy-DNA-6-21 stock, (RNA114.27) annealed to (p-ethoxy/DNA 6-21), chimeric, Peak at 9.43 minutes, (RNA) and peak at 7.5–8.5, p-ethoxy-DNA 6-21.
Figure 4B:
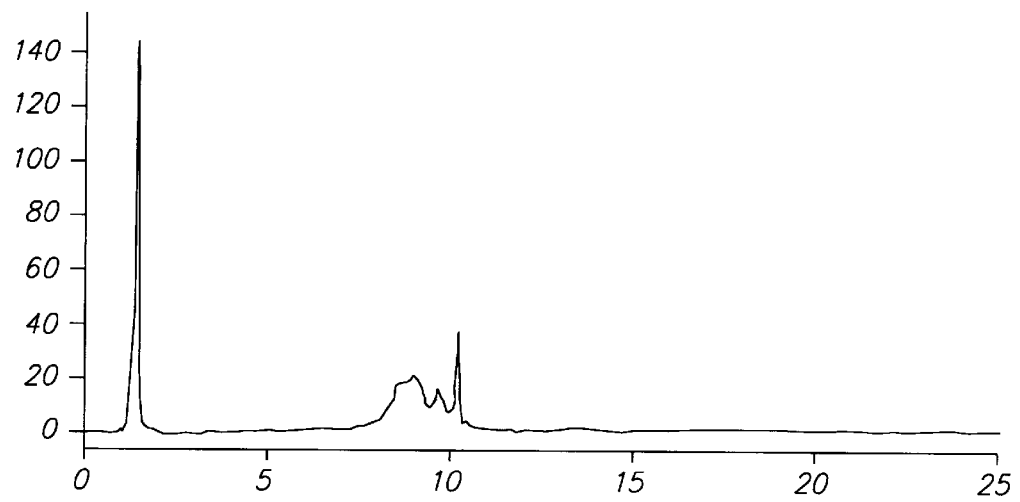
FIG. 4b is an HPLC graph of RNA vs p-ethoxy-DNA-6-21 and RNaseH buffer only, (RNA114.27) and (p-ethoxy-DNA 6-21), duplex incubated in RNaseH buffer 30 minutes, peak at 10.0 minutes (RNA), peak at 8.9 minutes (p-ethoxy-DNA 6-21).
Figure 4C:
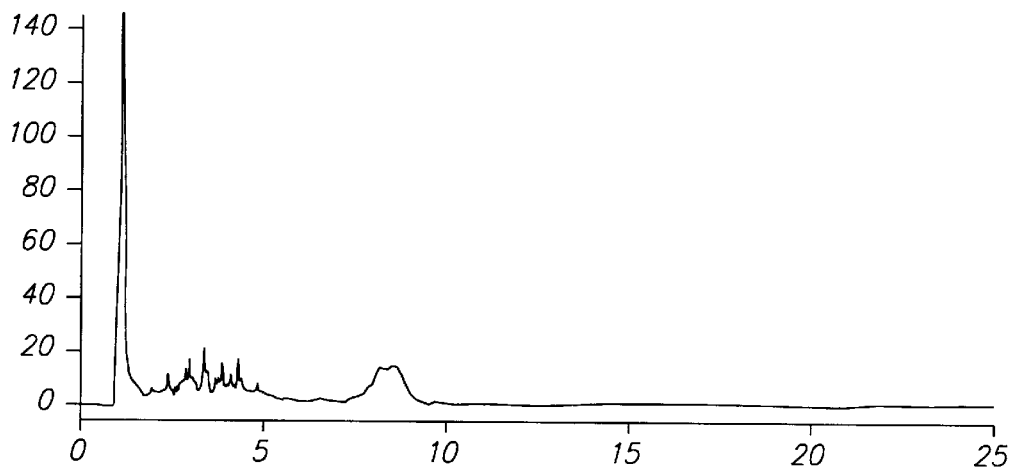
FIG. 4c is an HPLC graph of RNA vs p-ethoxy-DNA-6-21 and RNaseH enzyme, (RNA114.27) and (p-ethoxy-DNA6-21), duplex incubated in RNaseH buffer and RNaseH for a 30 minute incubation. Peak at 8–9 minutes (p-ethoxy-DNA-6-21), peaks at 2–5 minutes. Degradation fragments, RNaseH sensitive.
Figure 5A:
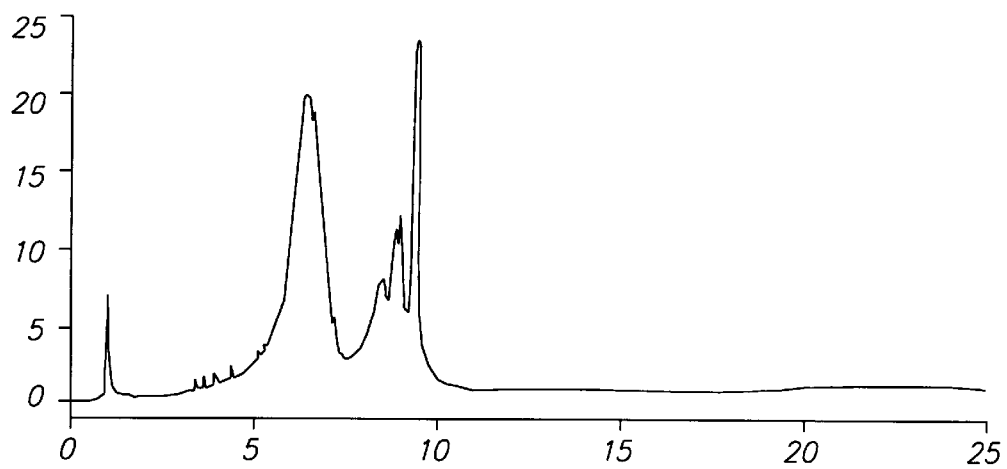
FIG. 5a is an HPLC graph of RNA vs. p-ethoxy stock, (RNA114.27) annealed to (p-ethoxy 114.27) (PBT)), peak at 9.4 minutes (RNA), peak at 5.5–7.5 minutes (PBT114.27).
Figure 5B:
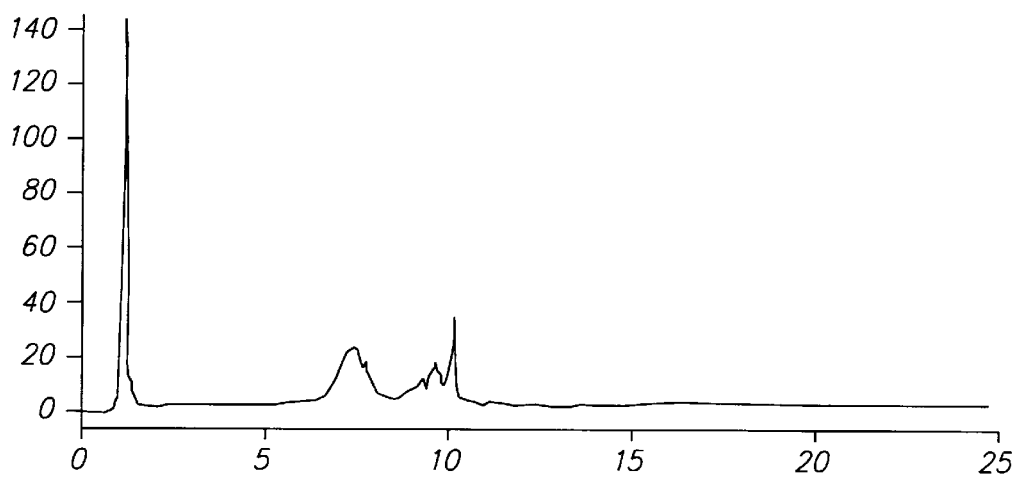
FIG. 5b is an HPLC graph of RNA vs. p-ethoxy and RNaseH buffer, (RNA114.27) and (PBT114.27), duplex incubated in RNaseH buffer 30 minutes, peak at 10.1 minutes (RNA), peak at 6.5–8 minutes (PBT).
Figure 5C:
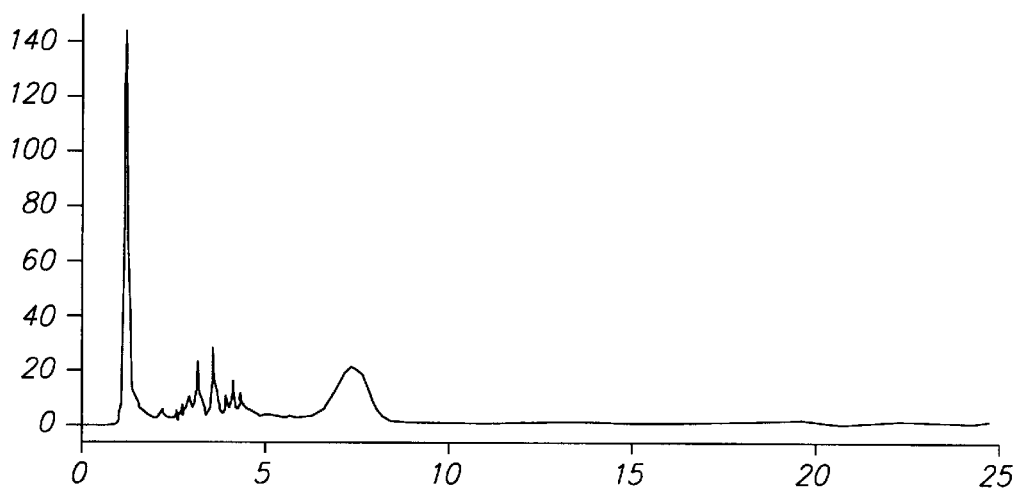
FIG. 5c is an HPLC graph of RNA vs. p-ethoxy and RNaseH enzyme, (RNA114.27) and (PBT114.27), duplex incubated in RNaseH buffer and RNaseH 30 minutes, peak at 6.5–8 minutes (PBT), peak at 2–5 minutes degradation fragments, RNaseH sensitive. (RNA is seen as a peak. In RNaseH+reactions, no peaks are seen, p-ethoxy will not run in a charged based system).

The bacterial RNaseH activation was observed in a number of experiments. The data were obtained after incubation of standards and controls. The data were also confirmed by capillary gel electrophoresis of the enzymatic digests as well as the controls involved in the experiments (FIGS. 1*d* and 1*e*). A time course study for 30 minutes in presence and absence of the enzyme RNaseH were carried out for RNA-DNA duplexes FIGS. 1*a* and 1*b* show the control experiment without RNaseH; FIG. 1*c* is with RNaseH ), DNA-Antisense DNA duplex identifier no. 114.27. FIGS. 2*a* and 2*b* shows the control experiment without RNaseH, FIG. 2*c* is with RNaseH, RNA-p-ethoxy DNA duplex identifier no. 9-9-9. FIGS. 3*a* and 3*b* are controls without RNaseH, FIG. 3*c* is with RNaseH, RNA-p-ethoxy DNA identifier no. 6–21. FIGS. 4*a* and 4*b* are controls without RNaseH, FIG. 4*c* is with RNaseH, RNA-p-ethoxy DNA duplex identifier no. 114.27. FIGS. 5*a* and 5*b* are controls without RNaseH. FIG. 5*c* is with RNaseH. The RNaseH sensitivity was observed strongly for the duplexes with p-ethoxy DNA identifier no. 99-9 (FIG. 3*c*), p-ethoxy DNA identifier no. 6-21 (FIG. 4*c*), and the p-ethoxy DNA identifier no. PBT 114.7 (FIG. 5*c*).

Growth Inhibition Data

Figure 6:
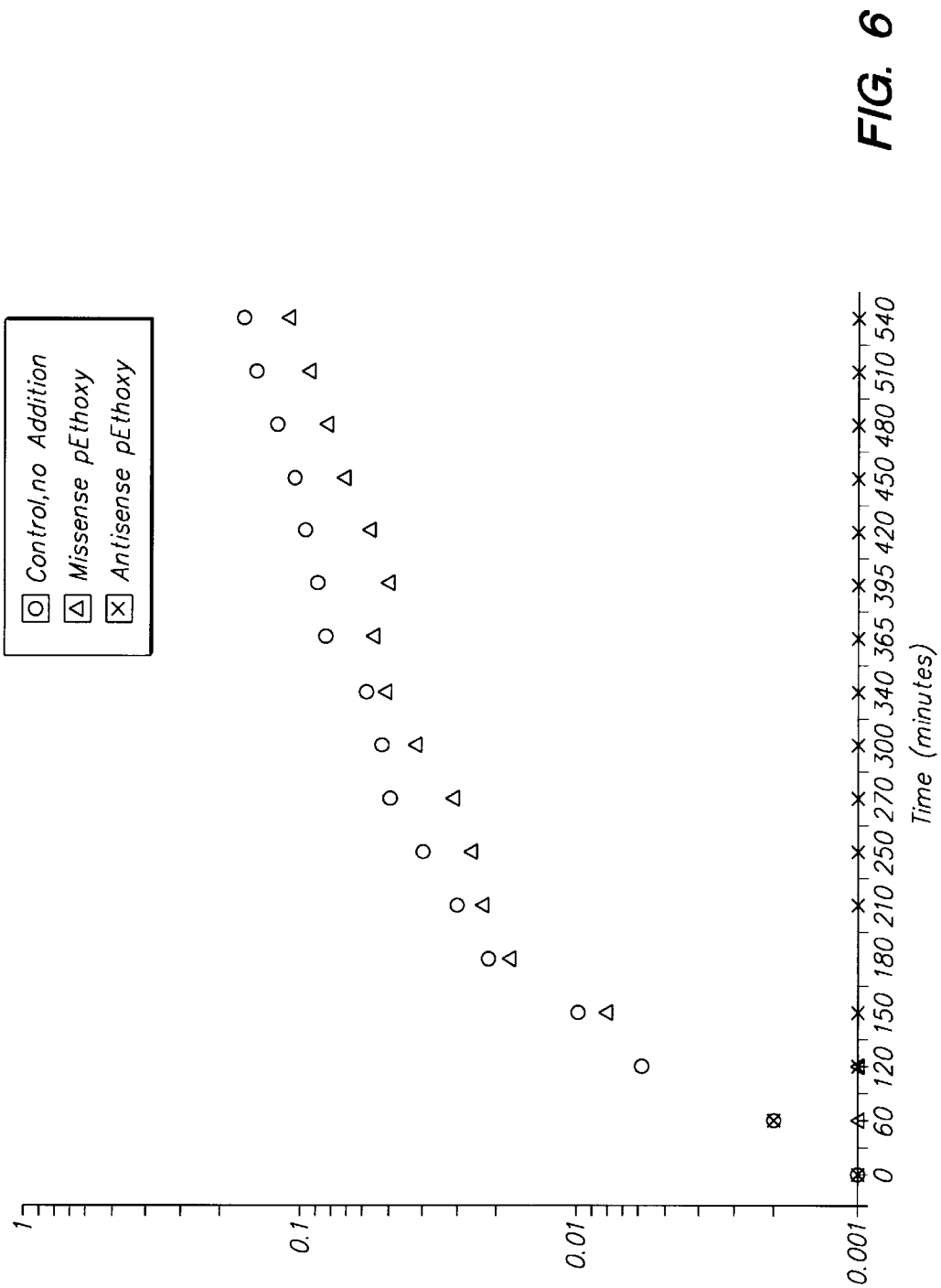
FIG. 6 shows a graph of growth inhibition of E. coli 35218 in the presence of p-ethoxy oligos; O is control, no addition of any oligonucleotide, ∧ is missense p-ethoxy, X is antisense p-ethoxy oligonucleotide.
Figure 7:
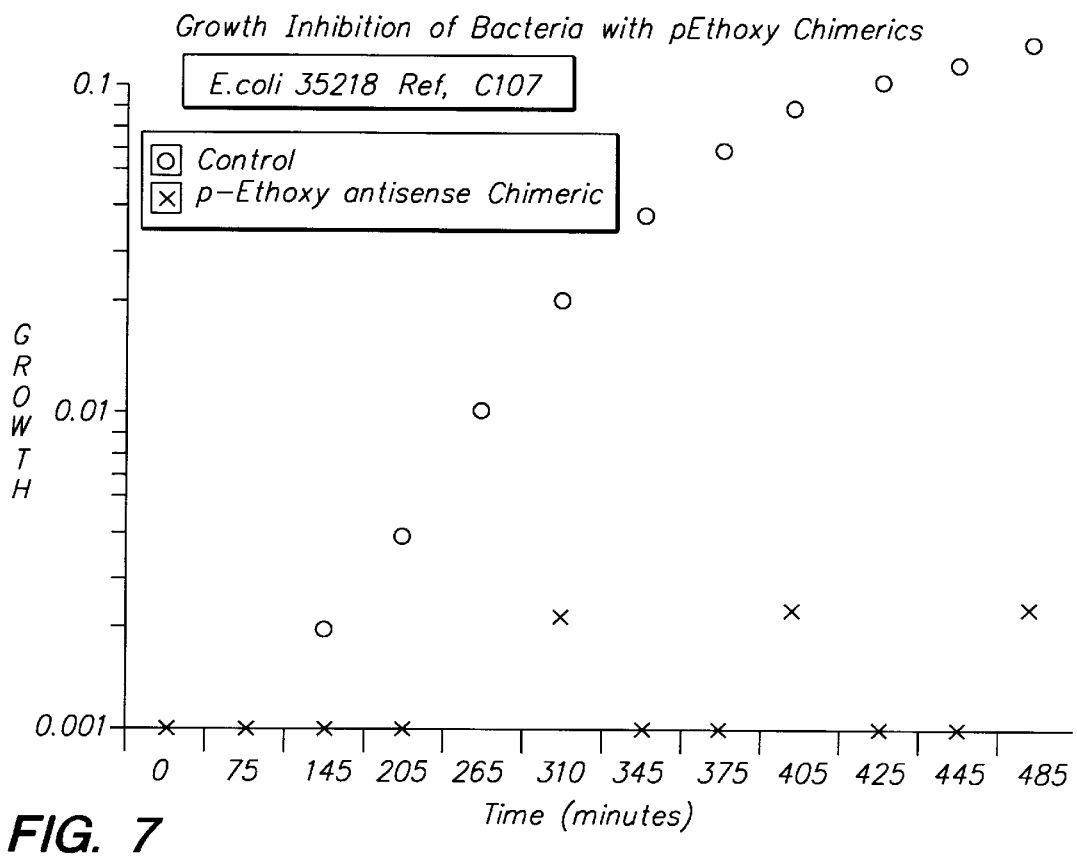
FIG. 7 shows a graph of growth inhibition of E. coli 35218 (Ref C107) with p-ethoxy chimerics; O is control, X is p-ethoxy chimera (identifier no. 5-18-4).
Figure 8:
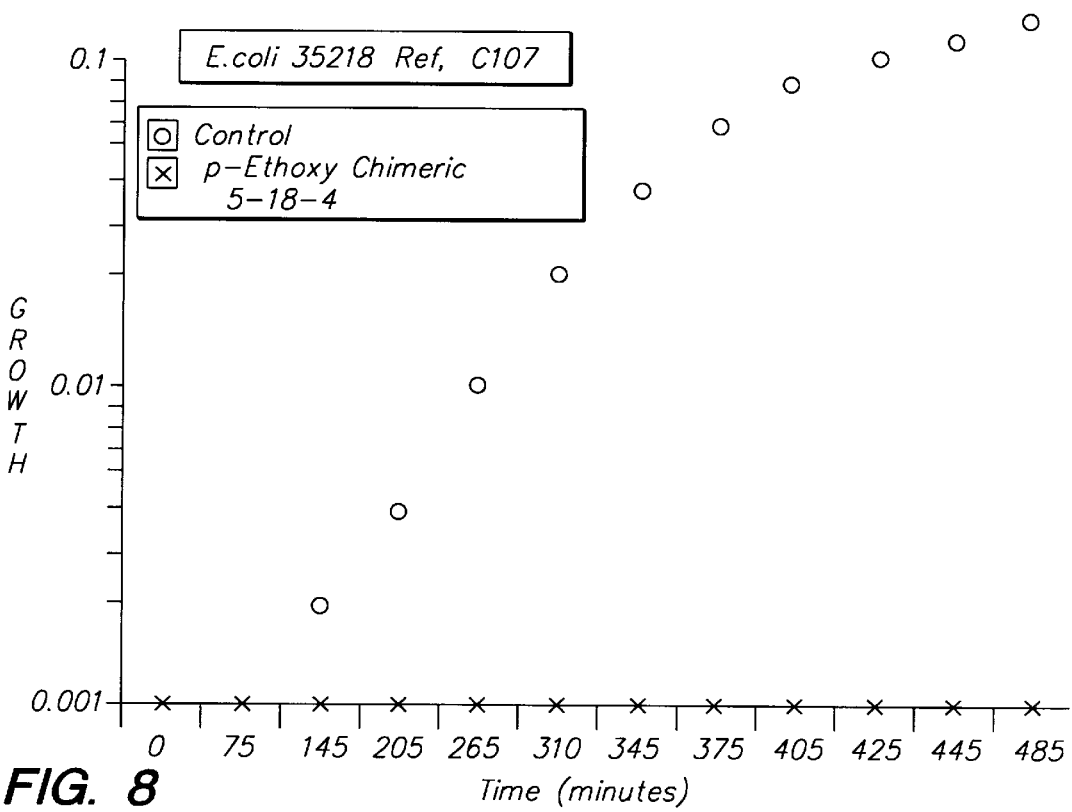
FIG. 8 shows a graph of growth inhibition study of E. coli 35218 by p-ethoxy chimerics; O is Control, with no oligonucleotide, X is p-ethoxychimera (identifier no. 9-9-9).
Figure 9:
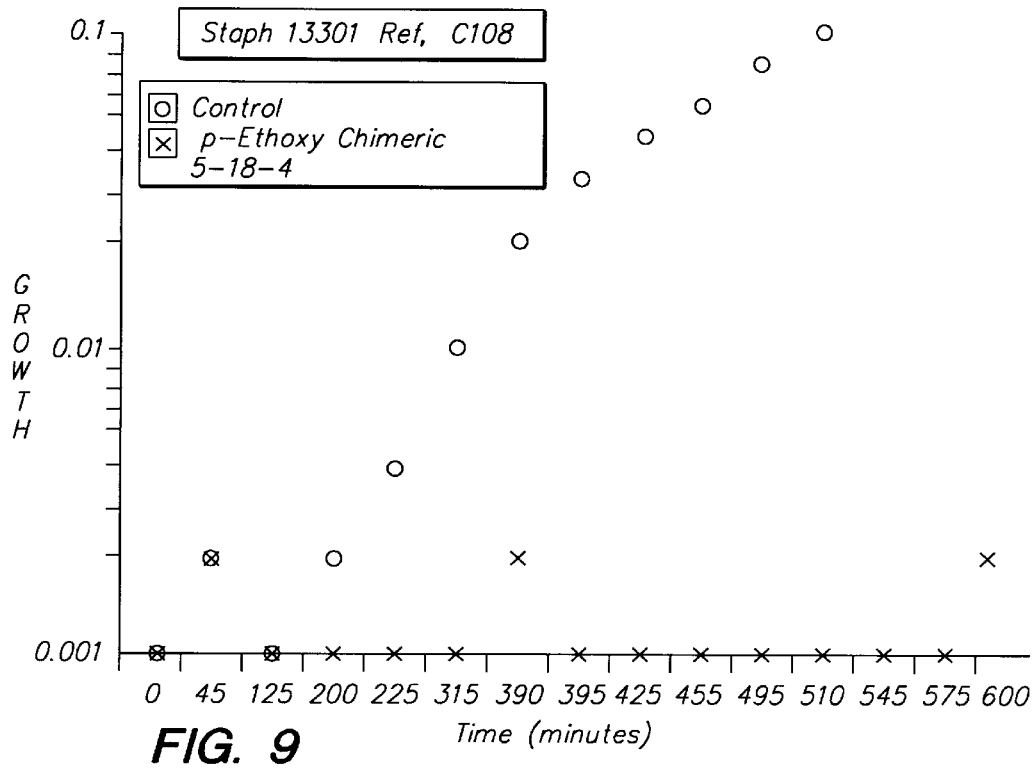
FIG. 9 shows a graph of growth inhibition of Staph 13301 (ref C108); O is Control, X is p-ethoxy chimeric no. 5-18-4.
Figure 10:
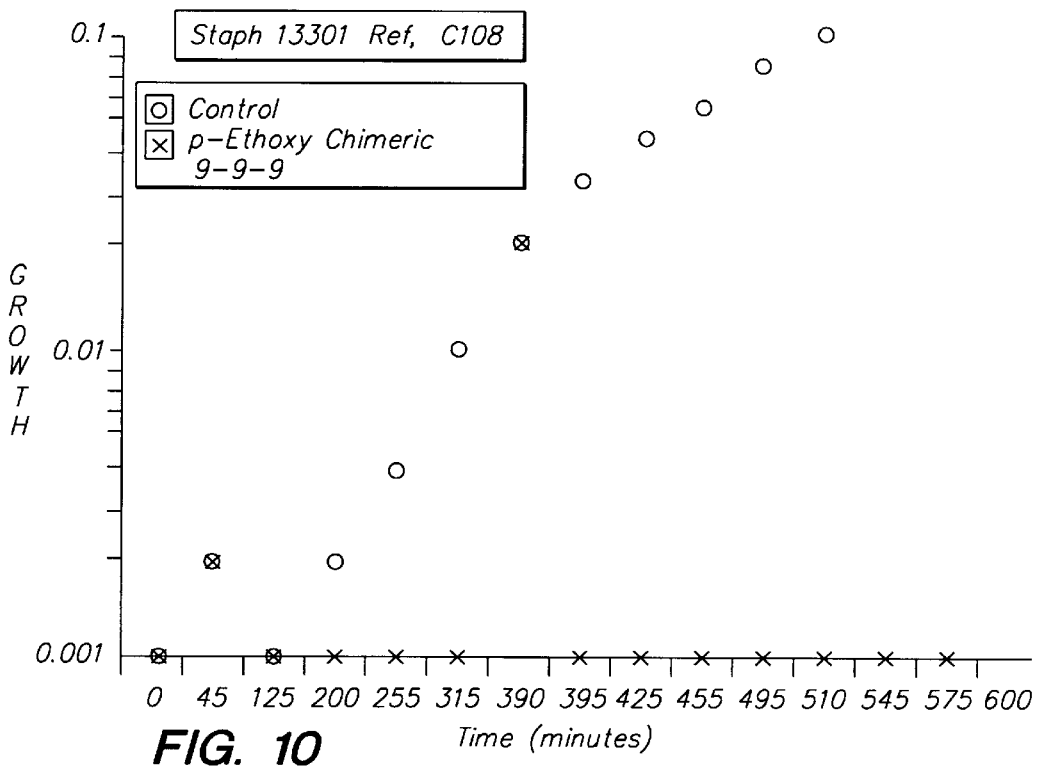
FIG. 10 shows a graph of growth inhibition of Staph 13301 (ref C108) by p-ethoxy chimera (no. 9-9-9); O is Control, X is p-ethoxy chimera 9-9-9.
Figure 11:
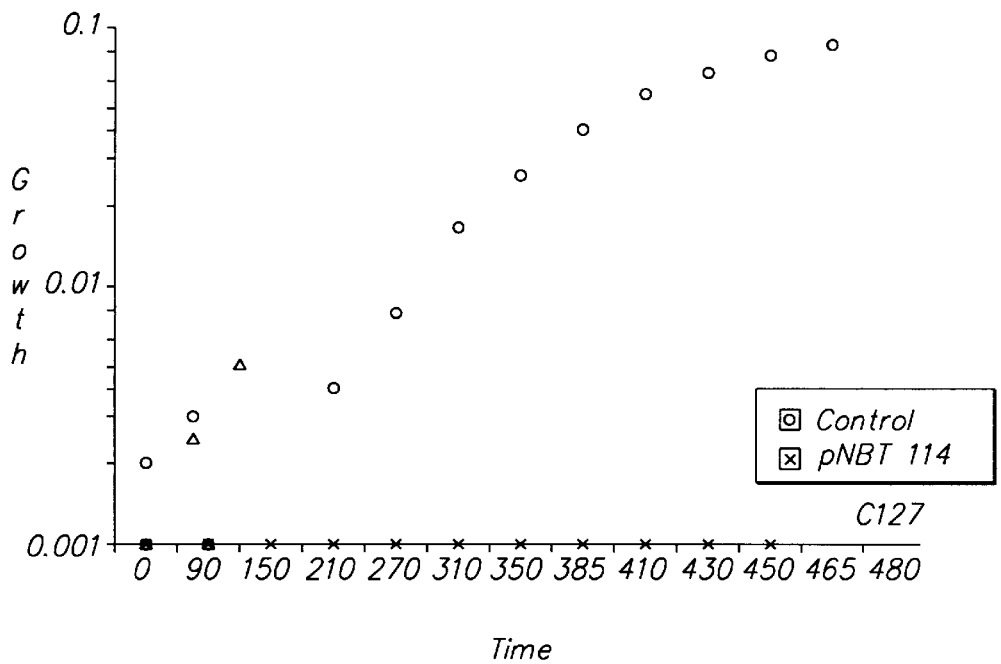
FIG. 11 shows a graph of growth inhibition of E. coli 35218 by p-ethoxy oligo p-NBT114; O is Control, X is p-NBT114.
Figure 12:
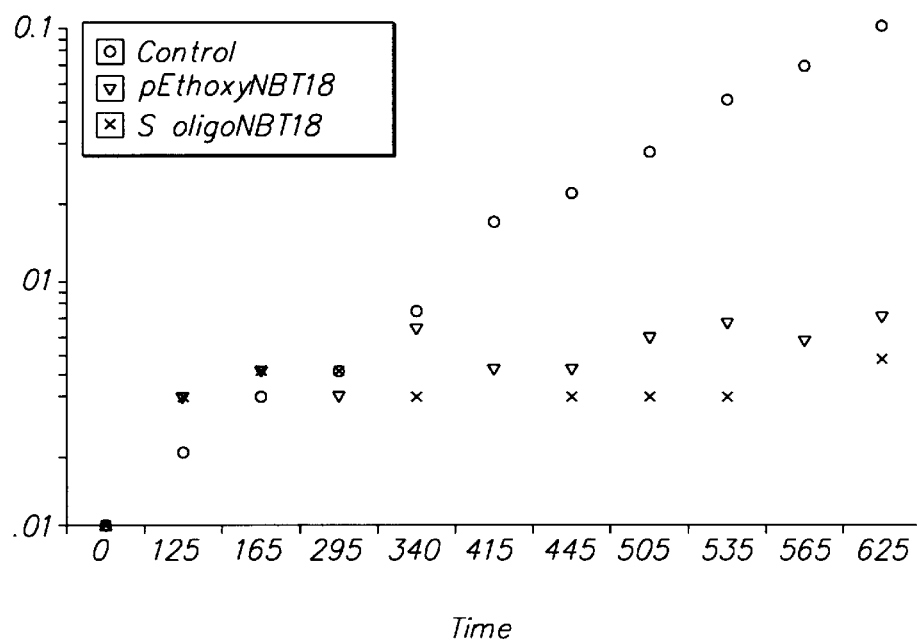
FIG. 12 shows a graph of comparative growth inhibition study of Staph 13301, between p-ethoxy oligonucleotide (identifer no. p-ethoxyNBT18) and phosphorothioate oligonucleotide (identifier no. S oligoNBT18); O is Control, X is p-ethoxyNBT18, ▽.is.S oligoNBT18.
Figure 13:
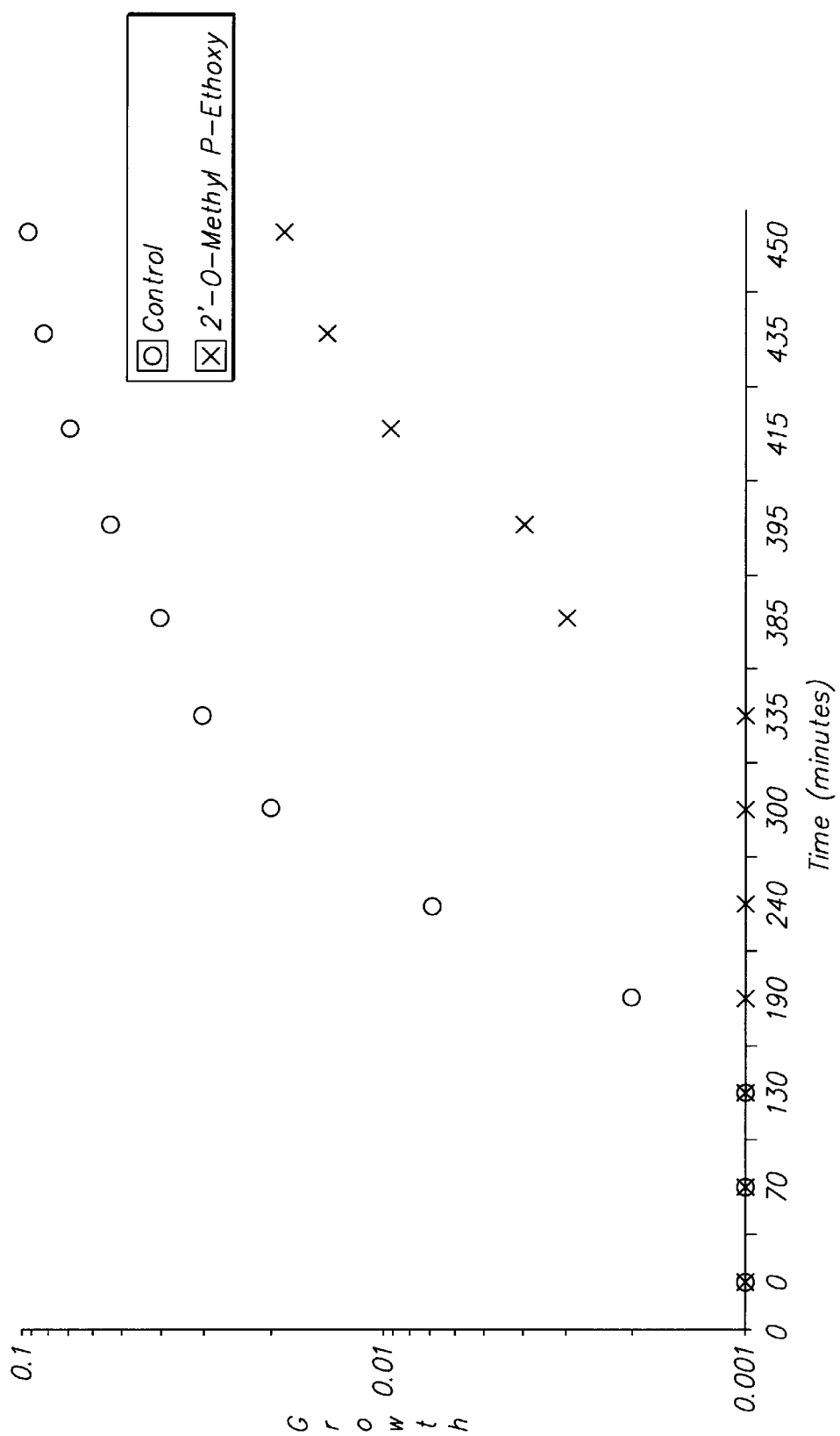
FIG. 13 shows a graph of growth inhibition of *E.coli* by p-ethoxy-2'-O-methyl oligonucleotide (Ref. C148); O is Control, X is 2'-O-methyl-p-ethoxy oligo (identifier no. POM114).

Growth inhibition of *E. coli* 35218 was performed in the presence of p-ethoxy oligos which are identifier numbers. During the course of 9 hours, the antisense p-ethoxy oligo was able to completely stop the growth of *E. coli* 35218. Under similar conditions, the missense p-ethoxy oligonucleotide was ineffective, similar to control with no addition of any oligonucleotide (See FIGS. 6 and 7). Essentially complete growth inhibition of bacteria (*E. coli* 35218, Ref C107) was demonstrated with p-ethoxy chimera (identifier no. 9-9-9) (see FIG. 8). Growth inhibition of Staph 13301, (ref C 108) took place almost completely with p-ethoxy chimera (identifier no. 5–184) (see FIG. 9), as well as with the p-ethoxy chimera (identifier no. 9-9-9) (see FIG. 10). Complete growth inhibition of *E. coli* 35216 was also observed with the p-ethoxy chimera (identifier no. pNBT 114) (see FIG. 11). The growth inhibition of Staph 13301 microorganism in the cell culture assay system by p-ethoxy oligo (p-ethoxy NBT 18) indicated significant inhibition. A comparative study of growth inhibition of Staph 13301 between the p-ethoxy oligonucleotide (identifier no. p-ethoxyNBT 18), and the corresponding phosphorothioate oligonucleotide (identifier no. S oligoNBT 18), showed that the p-ethoxy oligo was superior to phosphorothioate oligo, and the effect was pronounced over a 24 hour period of growth. The phosphorothioate oligonucleotide (identifier no. S oligo NBT 18) was also less effective during the initial 10 hour period (see FIG. 12). Growth inhibition studies of *E. coli* were also carried out with p-ethoxy-2'-O-methyl oligonucleotides, and almost complete inhibition was observed in a experiment during the initial 5.5 hours (see FIG. 13).

Cell culture studies were also performed using critical "cross-over" design, consisting of Luciferase assay system in which the specificity of inhibition of the target fusion is confirmed by comparison to a non-target fusion. In control experiments, the target was deleted from the luciferase constructs. Oligonucleotide chimeras with the 2'-O-methyl hybridizing arm were found to have reduced antisense activity in cell culture system. This may be due to the exonuclease degradation of the 2'-O-methyl phosphodiester linkages. Oligonucleotide of the present invention, consisting of 2'-O-methyl-p-ethoxy as part of the backbone were tested for similar activity.

Figure 14:
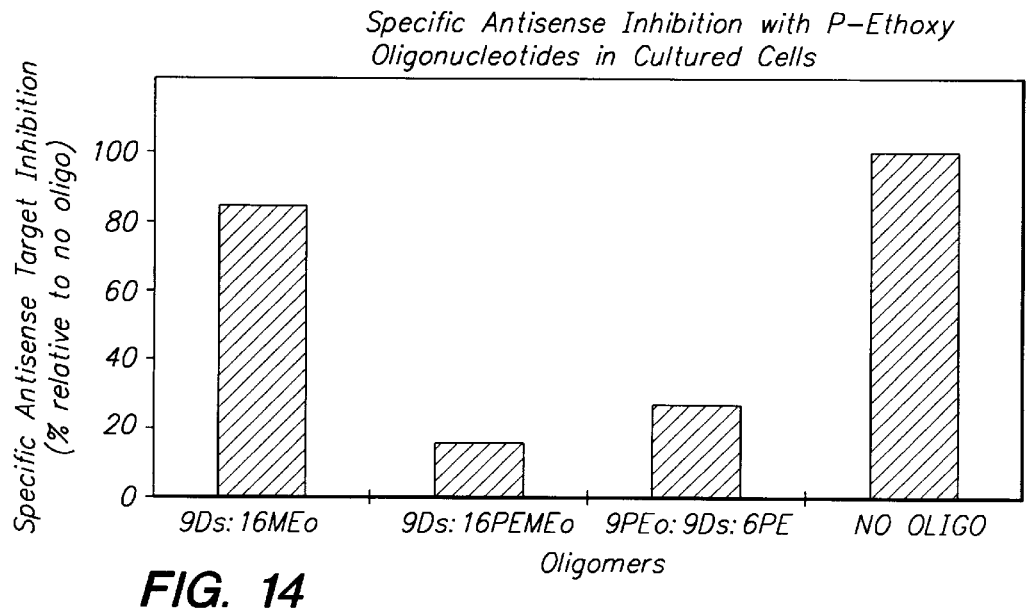
FIG. 14 shows a histogram of specific inhibition of cultured cells by luciferase fusion method by the oligonucleotides containing p-ethoxy as well as 2'-O-methyl backbone.

In the present invention, the inventors demonstrated that a 25-mer oligonucleotide containing 9-phosphorothioate linkages at the 5'-terminus, followed by sixteen 2'-O-methyl linkages (identifier no. 9Ds:16MEo) showed little or no specific inhibition of the targeted luciferase fusion. The p-ethoxy containing chimeras inhibited the targeted luciferase fusion by 83% (identifier no. 9Ds:16PEMEo) and 71% (identifier no. 9PEo:9Ds:6PE) (see FIG. 14 and Example 2).

Thermal Melting Studies with the p-Alkoxy Oligonucleotides 20-mer p-ethoxy oligodeoxynucleotides (example: oligo identifier no. PE 20) were hybridized with complementary DNA and RNA. Similarly p-ethoxy-2'-Omethyl oligonucleotides (example: 20-mer, oligo identifier no. RC 20) was hybridized with complementary RNA. As expected, the p-ethoxyoligodeoxynucleotide lowered the Tm of the DNA-DNA hybrid. However, the Tm enhancement of approximately 5–7° C. was observed with the p-ethoxy-2'-O-methyl oligonucleotide RNA-RNA hybrid, as compared to the DNA-DNA and DNA-RNA hybrids (see table 2).

TABLE 2

Thermal Melting Data

| Complementary Strands | | Tm (C) ** | % Hyperchromacity |
|---|---|---|---|
| C20–R20 | DNA-DNA | 62 | 22.90% |
| RC20–R20 | RNA-DNA | 66 | 23% |
| C20–PE20 | DNA-P-ethoxy | 55 | 21.60% |
| RC20–PE20 | RNA-P-ethoxy | 56 | 24.30% |
| POM–RC20 | | 71 | 20% |

** The Tm was determined in 50 mM NaCl, 5 mM/ pH 7.2, and 50 mM sodium phosphate.

Confirmation of Antisense Activity of Chimeras in Luciferase Assay System

A critical "cross-over" design was used in which the specificity of inhibition of the target fusion is confirmed by comparison to a non-target fusion. The inhibition seen with the p-ethoxy containing oligomers is target specific, as the inhibition shown is relative to a control luciferase construct with the target deleted. Additionally, the luciferase activity was normalized to an internal b-galactosidase co-receptor to account-for varying transfection efficiencies.

These positive results in cell culture show that the p-ethoxy linkage is sufficiently stable against nuclease to function in cells. These experiments show that the p ethoxy linkage is able to hybridize to its target site in cells. Thus, this linkage should be useful in steric blocking of RNA processing (splicing, translations, capping, poly adenylation) without the need for a phosphorothioate gap to activate RNaseH. This linkage should also be useful for triplex inhibition of gene transcription in cells.

The following examples are provided to enable those skilled in the art to practice the invention. These examples should not be considered limitations upon the scope of the invention, but merely as being illustrative and representative thereof.

EXAMPLES

Example 1

Structure 1a–1d.

In the oligonucleotide Structures 1a–1d, n is 0, and has a phosphate triester back bone alkyl phosphate ester group (R'). The alkyl group is methyl (structure 1a), ethyl (structure 1b), isopropyl (structure 1c), propyl (structure 1d), or a higher homolog thereof. B, B', B" includes, but is not limited to, natural nucleobases, adenine, cytosine, guanine, thymine, inosine, or an analog thereof, and uncommon or modified nucleobases, such as, but not limited to, 5-methylcytosine, 5-azacytosine, 5-halogen substituted (F, Cl, Br, I) uracil, cytosine, and 5-alkyl substituted, such as, but not limited to, C-5 propyne uracil and C-5 propyne cytosine.

Structure 1

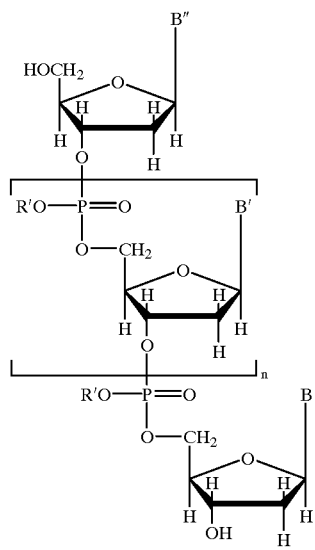

Structure 2(a–d).

In the oligonucleotide Structure 2(a–d), n=1–60, and has at least one phosphate alkyl triester group (R'). The alkyl group is methyl (structure 2a), ethyl (structure 2b), isopropyl (structure 2c), propyl (structure 2d), or a higher homolog thereof. The other phosphate group (R") includes, but is not limited to, $OCH_3$ (p-methoxy), $OC_2H_5$ (p-ethoxy), H (natural phosphodiester), S (phosphorothioate), S—P=S (phosphorodithioate), $CH_3$ (methyl phosphonate), $—NR_2$ (phosphoramidate). B, B', B" includes, but not limited to natural nucleobases, such as adenine, cytosine, guanine, thymine, inosine, or an analog thereof, and uncommon nucleobases, such as but not limited to, 5-methylcytosine, 5-azacytosine, 5-halogen substituted (F, Cl, Br, I) uracil and cytosine, and 5-alkyl substituted such as, but not limited to, C-5 propyne uracil and C-5 propyne cytosine.

Structure 2

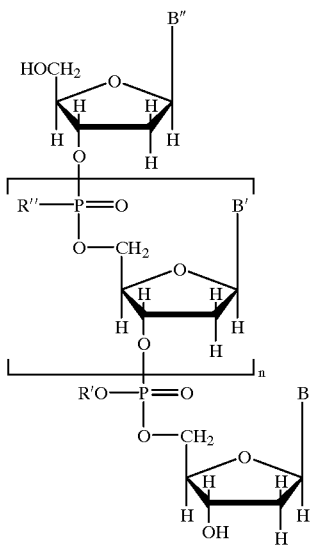

Structure 3(a–d).

In the oligonucleotide Structures 3a–3d, n is 0, and has a phosphate alkyl ester backbone (R'). The alkyl group (R') is methyl (Structure 3a), ethyl (Structure 3b), isopropyl (Structure 3c), or propyl (Structure 3d). The 2'-hydroxyl is modified to 2'-O-methyl group as part of the modified sugar backbone. B, B', B" includes, but is not limited to, natural nucleobases, such as adenine, cytosine, guanine, thymine, inosine, or analog thereof, and uncommon nucleobases, such as, but not limited to, 5-methylcytosine, 5-azacytosine, 5-halogen substituted (F, Cl, Br, I) uracil, and cytosine, and 5-alkyl substituted nucleobases, such as, but not limited to, C-5 propyne uracil and C-5 propyne cytosine.

Structure 3

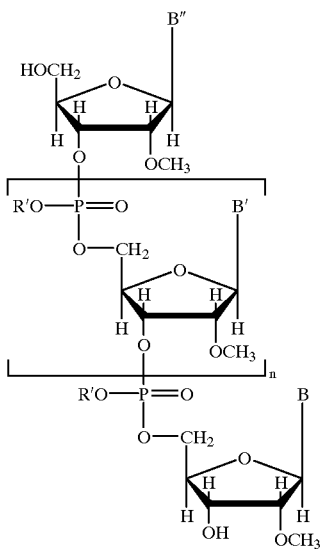

Structure 4(a–d).

In the oligonucleotide Structures 4a–4d, n is 1–60, and 2'-hydroxyl is modified as methyl group as part of the modified sugar backbone with R' as one of the phosphate alkyl ester backbone. The alkyl group (R') is methyl (structure 4a), ethyl (structure 4b), or isopropyl (4c), propyl (4d), or a higher homolog thereof. The other phosphate group (R") may be, but is not limited to, $OCH_3$(p-methoxy), $OC_2H_5$(p-ethoxy), HO— (natural phosphodiester), S (phosphorothioate), S—P=S (phosphorodithioate), $CH_3$ (methyl phosphonate), and $NR_2$(phosphoramidate). B, B', B" includes, but is not limited to, natural nucleobases, such as adenine, cytosine, guanine, thymine, inosine, and analogs thereof, and uncommon nucleobases, such as, but not limited to, 5-methylcytosine, 5-azacytosine, 5-halogen substituted (F, Cl, Br, I) uracil and cytosine, and 5-alkyl substituted, such as, but not limited to, C-5 propyne uracil and C-5 propyne cytosine.

Structure 4

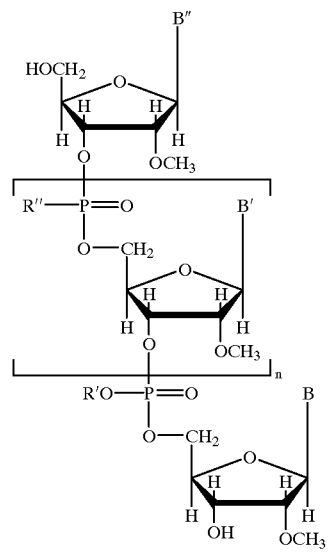

Structure 5(a–d).

In the oligonucleotide Structures 5a–5d, n is 0, where the $OR_3$ group is a 2'-modified sugar backbone, and R' is one of the phosphate alkyl ester groups. The alkyl group is methyl (structure 5a), ethyl (structure 5b), isopropyl (structure 5c), propyl (structure 5d), or the higher homolog thereof. The $OR_3$ group may be, but is not limited to, methyl, ethyl, propyl, allyl. B, B', B" includes, but is not limited to, natural nucleobases, adenine, cytosine, guanine, thymine, inosine or analogs thereof, and uncommon or modified nucleobases, such as, but not limited to 5-methylcytosine, 5-azacytosine, 5-halogen substituted (F, Cl, Br, I) uracil, cytosine, and 5-alkyl substituted, such as, but not limited to, C-5 propyne uracil and C-5 propyne cytosine.

In the oligonucleotide Structures 5a–5d, n is 1–60, where R' is one of the phosphate alkyl ester groups. The alkyl ester group (R') could be methyl (structure 5a), ethyl (structure 5b), isopropyl (structure 5c), propyl (structure 5d), or a higher homolog thereof. The other phosphate group (R") may be, but not limited to OH (natural phosphodiester), $OCH_3$, $OC_2H_5$, $isoOC_3H_7$, $OC_3H_7$, S (phosphorothioate), S—P=S (phosphorodithioate), $CH_3$ (methyl phosphonate), —NR'R" (phosphoramidate). The 2'-hydroxyl group ($OR_3$) is substituted with alkyl groups such as, but not limited to, ethyl, propyl, and allyl groups. B, B', B" includes, but is not limited to, natural nucleobases, such as adenine, cytosine, guanine, thymine, inosine, or analogs thereof, and uncommon nucleobases, such as but not limited to, 5-methylcytosine, 5-azacytosine, 5-halogen substituted (F, Cl, Br, I) uracil and cytosine, and other 5-alkyl substituted such as, but not limited to, C-5 propyne uracil, and C-5 propyne cytosine.

Structure 5

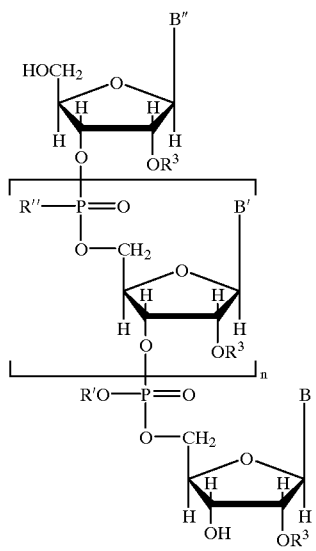

Structure 6(a–d)

In the oligonucleotide Structures 6a–6d, n is 0, where X is a 2'-modified sugar backbone, and R' is one of the phosphate alkyl ester groups. The alkyl ester is methyl (structure 6a), ethyl (structure 6b), isopropyl (structure 6c), propyl (structure 6d), or a higher homolog thereof. The X group includes, but is not limited to, halogen (F, Cl), or substituted amino group (NR'R"). B, B', B" includes, but is not limited to natural nucleobases, adenine, cytosine, guanine, thymine, inosine, and analogs thereof, and uncommon or modified nucleobases, such as, but not limited to 5-methylcytosine, 5-azacytosine, 5-halogen substituted (F, Cl, Br, I) uracil, cytosine, and 5-alkyl substituted, such as, but not limited to, C-5 propyne uracil and C-5 propyne cytosine.

In the oligonucleotide Structures 6a–6d, n is 1–60, and R' is a phosphate alkyl ester group. The alkyl ester group (R') is methyl (structure 6a), ethyl (structure 6b), isopropyl (structure 6c), propyl (structure 6d), or a higher homolog thereof. The other phosphate group R" may be, but is not limited to —OCH$_3$(methoxy), —OC$_2$H$_5$(ethoxy), iso-OC$_3$H$_7$ (isopropoxy), —OC$_3$H$_7$ (propoxy), —OH (phosphodiester), S(phosphorothioate), S—P=S (phosphorodithioate), CH$_3$ (methyl phosphonate), —NR'R" (phosphoramidate). The 2'-position is substituted with group (X). The X group may be, but is not limited to F, Cl, a —NR'R" group. The nucleobase B, B', B" includes, but not limited to, natural nucleobases, such as adenine, cytosine, guanosine, thymine, inosine, or analogs thereof, and uncommon nucleobases, such as, but not limited, to 5-methylcytosine, 5-azacytosine, 5-halogen substituted (F, Cl, Br, I) uracil and cytosine, and 5-alkyl substituted such as, but not limited to C-5 propyne uracil and C-5 propyne cytosine.

Structure 6

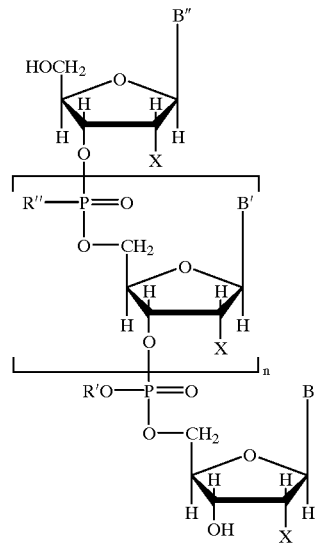

Structure 7(a–d)

In the oligonucleotide Structures 7a–7d, n is 0, with one phosphate alkyl ester group (R'). The alkyl ester group (R') is methyl (structure 7a), ethyl (structure 7b), isopropyl (structure 7c), propyl (structure 7d), or a higher homolog thereof. B, B', B" includes, but is not limited to natural nucleobases, such as adenine, cytosine, guanosine, thymine, inosine, and analogs thereof, and uncommon nucleobases, such as but not limited to, 5-methylcytosine, 5-azacytosine, 5-halogen substituted (F, Cl, Br, I) uracil and C-5 alkyl substituted such as, but not limited to, C-5 propyne uracil and C-5 propyne cytosine. The phosphodiester linkage in these oligonucleotides is 3'-3', preferably with thymidine nucleoside at the 3'-terminus of the oligonucleotides.

In the oligonucleotide Structures 7a–7d, n is 1–60, with one of the phosphate alkyl ester groups (R'). The alkyl ester group (R') may be methyl (structure 12a), ethyl (structure 12b), isopropyl (structure 12c), propyl (structure 12d), or a higher homologs thereof. The other phosphate group (R") may be, but is not limited to —OH (natural phosphodiester), —OCH$_3$(methoxy), —OC$_2$H$_5$ (ethoxy),—isoOC$_3$H$_7$ (isopropoxy), —OC$_3$H$_7$ (propoxy), —S, —(S)$_2$, —CH$_3$, —NR'R". B, B', B" includes, but is not limited to, natural nucleobases, such as adenine, cytosine, guanosine, thymine, inosine, or analogs thereof, and uncommon nucleobases, such as, but not limited to, 5-methylcytosine, 5-azacytosine, 5-halogen substituted (F, Cl, Br, I) uracil and cytosine, C-5 alkyl substituted such as, but not limited to, C-5 propane uracil and C-5 propyne cytosine. The phosphodiester linkage in these oligonucleotides is 3'-3', preferably thymidine, at the 3'-terminus of the oligonucleotides.

Structure 7

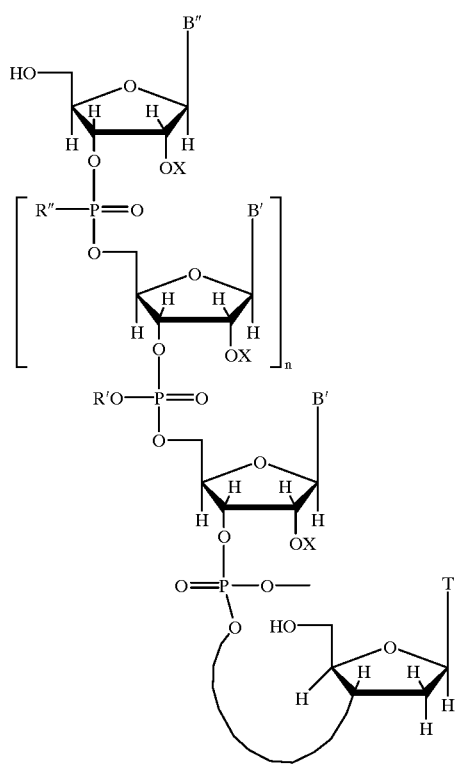

Synthesis of p-ethoxy-2'-deoxy-oligonucleotides. The schematic below directs the synthesis of sequences C20-PE20). The nucleoside phosphoramidites, structures 8–11, were used in this discovery).

Structures (8–11)

N-PAC-5'-DMT Deoxynucleoside-N,N-Diisopropyl p-Ethoxy phosphoramidites (For Synthesis of Neutral Charge p-Ethoxy DNA Oligomers)

(8)

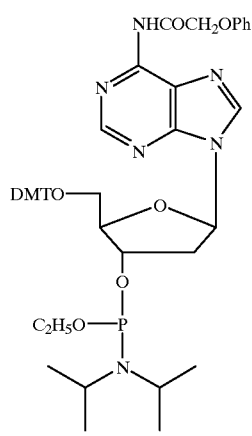

(9)

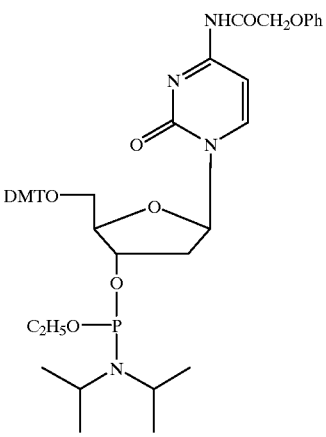

(10)

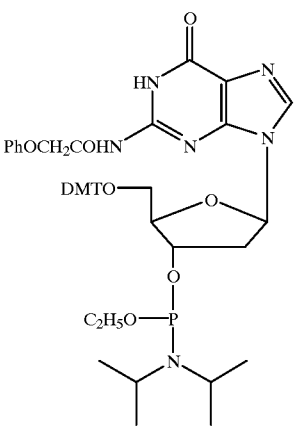

(11)

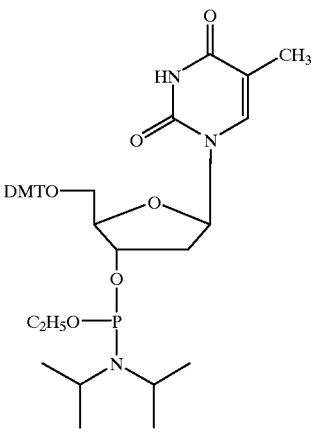

Synthesis of p-ethoxy-2'-O-methyloligonucleotides. The synthesis of these oligonucleotides was carried out by utilizing the structures 12–15. These structures have been described in the U.S. Pat. No. 5,525,719, incorporated herein in its entirety, for the purpose of synthesis of p-alkoxy modified oligonucleotides.

Structures (12–15)

N-PAC-5'-DMT Ribonucleoside-N,N-Diisopropyl p-Ethoxy 2'-O-Methyl phosphoramidites (For synthesis of Neutral Charge p-Ethoxy 2'-O-Methyl oligomers)

(12)
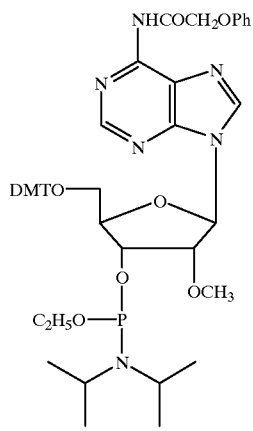

(13)
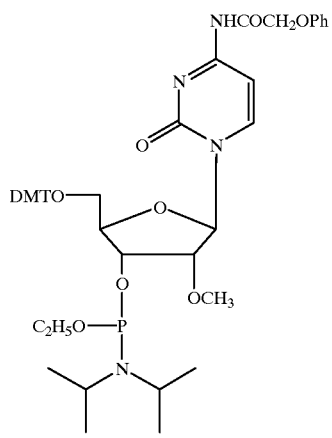

(14)
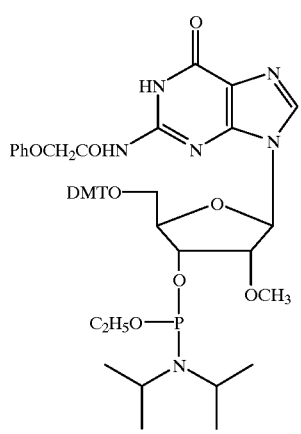

(15)
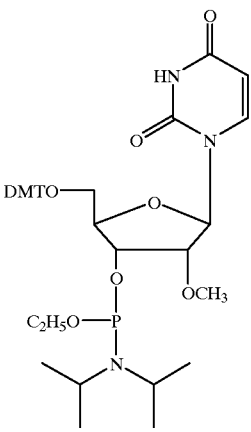

Synthesis of p-isopropoxy-2'-deoxyoligonucleotides. The synthesis of these oligonucleotides was carried out by utilizing the structures 16–19.

Structures (16–19)

N-Protected-5'-DMT Deoxynucleoside-N,N-Diisopropyl p-isopropoxy phosphoramidites (For Synthesis of Neutral Charge p-isopropoxy DNA Oligomers)

(16)
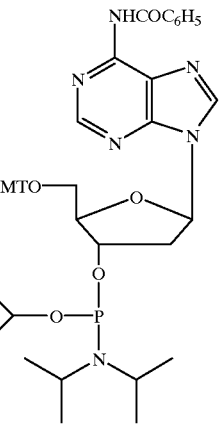

(17)
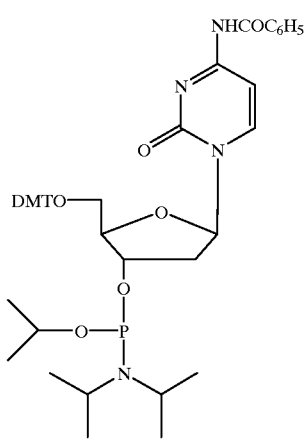

-continued

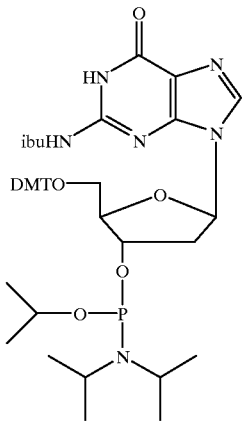

(18)

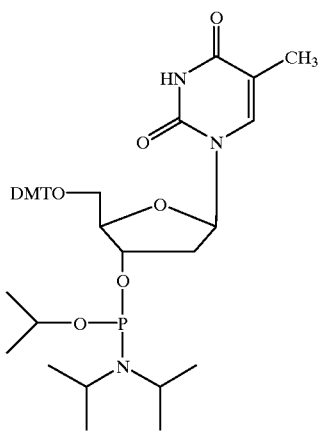

(19)

Deprotection of base protecting groups from the fully protected p-alkoxy oligomers.

Figure 15:
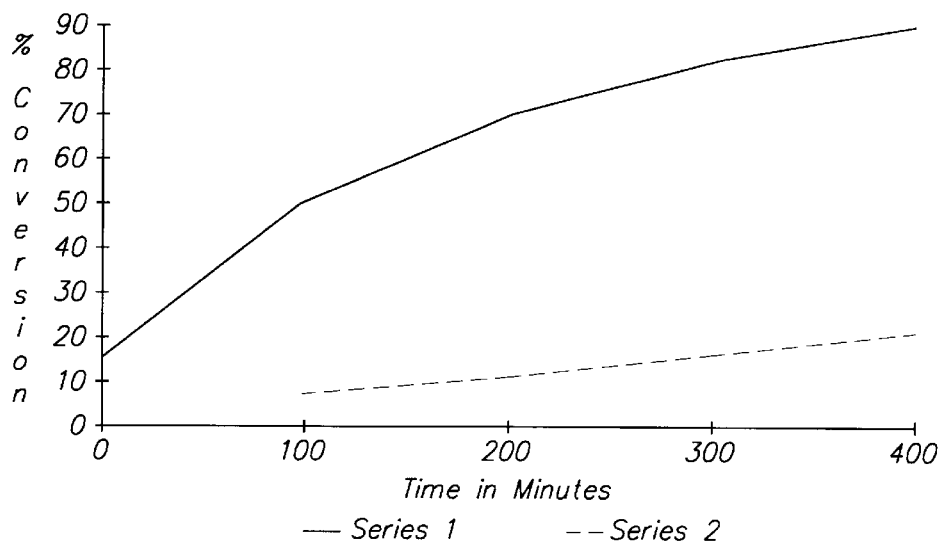
FIG. 15 shows a graph of NH3/Pyridine reaction on standard base protected p-ethoxy oligonucleotides (17 mer). Series 1 is the full length base deprotected p-ethoxy oligonucleotides. Series 2 is base and phosphate deprotected oligomer species.

FIG. 15 and FIG. 16 show graphically the behavior of the base protecting groups and the stability of the p-alkoxy groups in the oligomers. Further purification of the pure oligomers was achieved by analytical HPLC as shown in Table 3.

TABLE 3

Phosphate Alkylated Oligonucleotides: Composition, HPLC analysis

| Oligo | R.T. | ~avg. | % PE | % PO4 Linkages |
|---|---|---|---|---|
| p18.15 | 6.988<br>7.088 | 7.00 | 100% | 0 |
| p18.15-C* | 7.257<br>7.39<br>7.49 | 7.39 | 93% | 7% |
| p18.15-C5* | 7.563 | 7.56 | 79% | 21% |
| p18.15-C5* | 7.718<br>7.835 | 7.77 | 65% | 35% |
| p18.15-C9* | 8.053<br>8.17<br>8.303 | 8.17 | 46% | 64% |
| p18.15-C15* | 8.618 | 8.62 | 0% | 100% |

*single oligo, but chimera
**Regular DNA

HPLC Analysis on NucleoPak Analytical Column; gradient solvent delivery system;
Phase A;0.03M NaClO$_3$,25 mM NaOH, 10% Acetonitrile-.Phase B; 0.4M NaClO$_3$, 25 mM NaOH, 10% Acetonitrile. The gradient was for over a period of 20 minutes from 15% to 35% acetonitrile in either phase A and phase B.

Example 2

Luciferase Assay System

Plasmid Constructs. The plasmid used for the studies contained a portion of the ras gene sequence fused to luciferase (Monia, B. P., et. al., *Journal of Biological Chemistry.* 267, 19954–19962 (1992)). The control luciferase plasmids did not contain the ras target sequence.

Cell Culture Assay. The cells were grown to 40–90% confluence inDMEM(10% FBS, supplemented with glutamine, penicillin and strptomycin on gelatin coated 24 well plates. The gelatin coating was necessary for the cells to remain adherent during the transfections. Prior to transfection the cells were washed twice with PBS (containing magnesium and calcium). Lipofectin was mixed gently and 6.6 ml was added for each millimeter of reduced serum medium (Opti-MEM, Gibco/BRL, Gaithsbeg, Md.). Oligomers were added from 50–100 mM concentrated stock to make a master mixture. The Opti-MEM/ Lipofectin/ oligomer solution was added to the cells and incubated for 4 hours (~0.5 mls for one well of a 24 well plate).

A target transfection mixture was prepared by first diluting Sml of lipofectin per ml of Opti-MEM and mixing. Next 5 mg of luciferase target and 5 mg of CMV β-galactosidase were added per millimeter of opti-MEM/lipofectin mixture. The transfection mixture was mixed gently and allowed to complex for ~15 minutes. The master mixture reduced error by assuring that the control and experimental cells received the exact same cationic lipid/plasmid complex. The oligonucleotide containing media was removed from the cells and replaced with growth media and incubated for an additional 9–18 hours. The cell were rinsed with calcium and magnesium free media and the media was removed. The plates were frozen at −70° C. for >20 minutes and 100–300 ml of reporter lysis buffer (Promega, Madison Wis.) was added. The cells were put through 2 more freeze thaw cycles, to assure complete lysis. Luciferase assays were preformed according to the manufacture's instructions (Promega, Madison Wis.) and luminescence was detected with a 96 well luminometer (Packard, Meriden Conn.). β-galactosidase assays were performed (Galacton Plus, Tropix) according to manufactures instructions and detected on the Packard luminometer.

Chimeric Oligonucleotide Configurations Used In The Luciferase Assay System

The following symbols are used in the chimeric oligonucleotide configurations:

*s is phosphorothioate, all other phosphodiester

*Underlined is 2'-O-methyl modified phosphodiester (MEo)

*Bold is p-ethoxy (PEo)

*Underlined and bold is p-ethoxy plus 2'-O-methyl (PEMEo)

*Not underlined is DNA 1. 9Ds:16MEo: Poor or no antisense inhibition (see FIG. 14)
   5'-TsTsGsCsCsCsAsCsAsCCGACGGCGCCCACCA
2. 9Ds:16MEPEo: Antisense Inhibition obtained (see FIG. 14)
   5'-TsTsGsCsCsCsAsCsAsCCGACGGCGCCCACCA
3. 9PEo:9Ds:6PEo:1Do: Antisense Inhibition obtained (see FIG. 14)
   5'-TTGCCCACAsCsCsGsAsCsGsGsCsGCCCACCA The 2'-O-methyl chimeric 9Ds:16MEo showed little or no specific inhibition of the targeted luciferase fusion. The p-ethoxy containing chimerics inhibit the targeted luciferase fusion by 83% 9Ds:16MEPEo and 71% (9PEo:9Ds:6PEo:1Do). The ras oligomers shown were transfected into cells as described in the methods section. For each oligonucleotide tested a luciferase reporter construct containing the ras target site was subsequently transfected. For each oligonucleotide tested a control luciferase construct without the ras target site was also transfected. The luciferase activity resulting from the transfections with the targeted ras reporter were divided by the activity from the control luciferase transfections. All luciferase values were normalized to the internal b-gal co-receptor, and the values of the no oligonucleotide control was defined as 100%. For this study, the average Standard Error of the Mean, % C.V.>15%. Six-fold replicas of the transfections were performed.

Although the foregoing invention has been described in some detail by way of illustration and example for puposes of clarity of understanding, it will be obvious to one skilled in the art that certain changes and modifications may be practiced within the scope of the appended claims.

What is claimed is:

1. A compound represented by the formula:

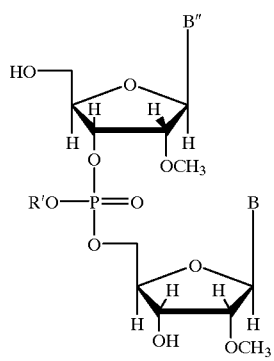

wherein O is oxygen; C is carbon, and H is hydrogen;

R' is part of an alkyl phosphate triester internucleosidyl group, and said R' is selected from the group consisting of methyl, ethyl, isopropyl, propyl and higher alkyl homologs to C-15; and B and B" are natural and modified nucleobase radicals selected from the group consisting of 9-adeninyl, 1-thyminyl, 1-cytosinyl, 9-guaninyl, 9-hypoxanthinyl, 1-(5-methylcytosinyl), 1-(5-azacytosinyl), 1-(5-bromouracilyl), 1-(5-bromocytosinyl), 1-(5-fluorouracilyl), 1-(5-fluorocytosinyl), 1-(5-chlorocytosinyl), 1-(5-chlorouracilyl), 1-(5-iodouracilyl), 1-(5-iodocytosinyl), 1-(5-propynyluracilyl) and 1-(5-propynylcytosinyl).

2. A compound represented by the formula:

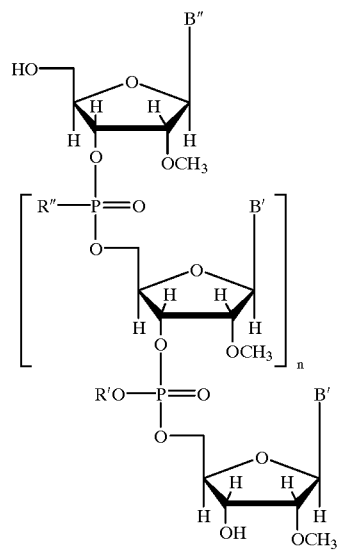

wherein n is 1–60;

O is oxygen; C is carbon, and H is hydrogen;

R' is part of an alkyl phosphate triesters located at the terminal 3' internucleosidyl position, and said R' is selected from the group of alkyl radicals consisting of methyl, ethyl, isopropyl, propyl and higher alkyl homologs up to C-15;

R" is selected from the group consisting of OH, $OCH_3$, $OC_2H_5$, $S^-$ and NR'''R'''' wherein N is nitrogen, R''' is a second alkyl radical selected from the group consisting of methyl, ethyl, propyl, isopropyl and alkyl homologs up to 16 carbons, and R'''' is a third alkyl radical selected from the group consisting of methyl, ethyl, propyl, isopropyl and alkyl homologs up to 16 carbons; and B, B' and B" are natural and modified nucleobase radicals selected from the group consisting of 9-adeninyl, 1-thyminyl, 1-cytosinyl, 9-guaninyl, 9-hypoxanthinyl, 1-(5-methylcytosinyl), 1-(5-azacytosinyl), 1-(5-fluorouracilyl), 1-(5-fluorocytosinyl), 1-(5-bromouracilyl), 1-(5-bromocytosinyl), 1-(5-chlorocytosinyl), 1-(5-chlorouracilyl), 1-(5-iodouracilyl), 1-(5-iodocytosinyl), 1-(5-propynyluracilyl) and 1-(5-propynylcytosinyl).

3. A compound represented by the formula:

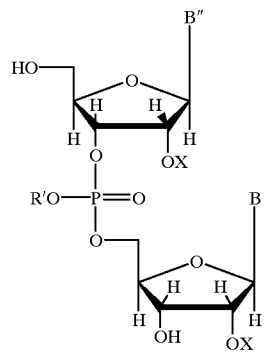

wherein O is oxygen; C is carbon, and H is hydrogen;

X is selected from the group consisting of ethyl, propyl, alkyl homologs up to 16 carbons and allyl;

R' is part of an alkyl phosphate triester group located at the internucleosidyl position, and said R' is an alkyl selected from the group consisting of methyl, ethyl, isopropyl, propyl and higher homologs up to C-15; and B and B" are natural and modified nucleobase radicals selected from the group consisting of 9-adeninyl, 1-thyminyl, 1-cytosinyl, 9-guaninyl, 9-hypoxanthinyl, 1-(5-methylcytosinyl), 1-(5-azacytosinyl), 1-(5-bromouracilyl), 1-(5-bromocytosinyl), 1-(5-fluorouracilyl), 1-(5-fluorocytosinyl), 1-(5-chlorouracilyl), 1-(5-chlorocytosinyl), 1-(5-iodouracilyl), 1-(5-iodocytosinyl), 1-(5-propynyluracilyl) and 1-(5-propynylcytosinyl).

4. A compound represented by the formula:

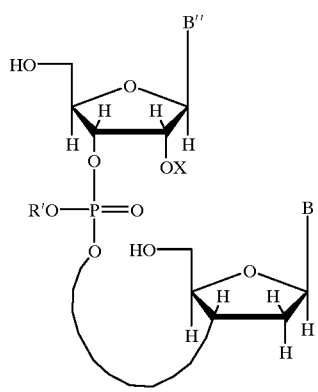

wherein O is oxygen; C is carbon, and H is hydrogen;

X is an alkyl group selected from the group consisting of methyl, ethyl, propyl, isopropyl and alkyl homologs up to C-15;

R' is part of an alkyl phosphate triesters located at the terminal 3' internucleosidyl position, and said R' is an alkyl selected from the group consisting of methyl, ethyl, isopropyl, propyl, and higher alkyl homologs up to C-15;

B and B" are natural and modified nucleobase radicals selected from the group consisting of 9-adeninyl, 1-thyminyl, 1-cytosinyl, 9-guaninyl, 9-hypoxanthinyl, 1-(5-methylcytosinyl), 1-(5-azacytosinyl), 1-(5-bromouracilyl), 1-(5-bromocytosinyl), 1-(5-fluorouracilyl), 1-(5-fluorocytosinyl), 1-(5-chlorouracilyl), 1-(5-chlorocytosinyl), 1-(5-iodouracilyl), 1-(5-iodocytosinyl), 1-(5-propynyluracilyl) and 1-(5-propynylcytosinyl).

5. A compound represented by the formula:

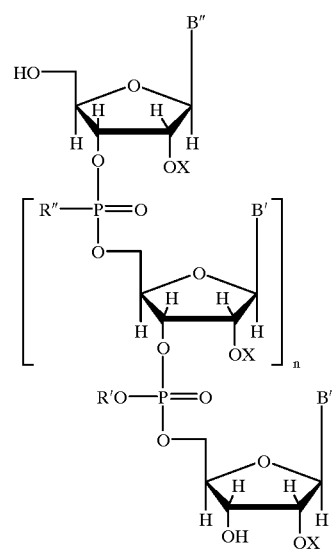

wherein n is 1–60;

O is oxygen; C is carbon, and H is hydrogen;

R' is part of an alkyl phosphate triester group located at the terminal 3' internucleosidyl position, and said R' is an alkyl group selected from the group consisting of methyl, ethyl, isopropyl, propyl and higher alkyl homologs up to C-15;

R" is selected from the group consisting of OH, $OCH_3$, $OC_2H_5$, $OC_3H_7$, O-iso $C_3H_7$, $S^-$, and NR'''R'''' wherein N is nitrogen, R''' is a second alkyl radical selected from the group consisting of methyl, ethyl, propyl, isopropyl and alkyl homologs up to 16 carbons, and R'''' is a third alkyl radical selected from the group consisting of methyl, ethyl, propyl, isopropyl and alkyl homologs up to 16 carbons;

X is selected from the group consisting of methyl, ethyl, propyl, isopropyl and higher alkyl homologs to C-15; and B, B' and B" are natural and modified nucleobase radicals selected from the group consisting of 9-adeninyl, 1-thyminyl, 1-cytosinyl, 9-guaninyl, 9-hypoxanthinyl, 1-(5-methylcytosinyl), 1-(5-azacytosinyl), 1-(5-bromouracilyl), 1-(5-bromocytosinyl), 1-(5-fluorouracilyl), 1-(5-fluorocytosinyl), 1-(5-chlorouracilyl), 1-(5-chlorocytosinyl), 1-(5-iodouracilyl), 1-(5-iodocytosinyl), 1-(5-propynyluracilyl) and 1-(5-propynylcytosinyl).

6. A compound represented by the formula:

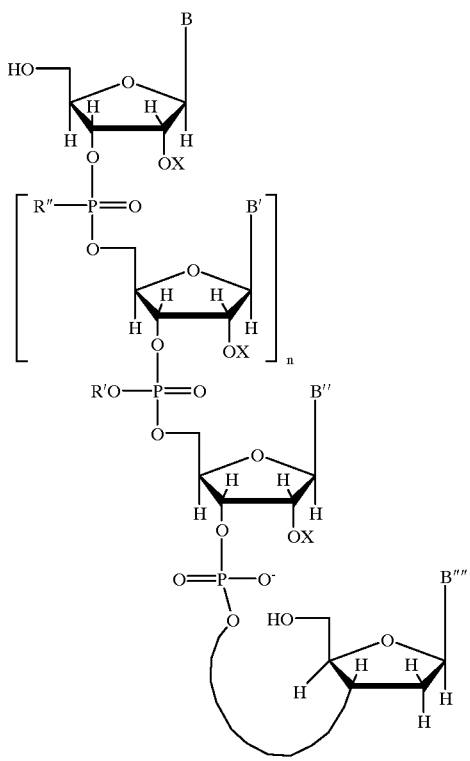

wherein n is 1–60;

wherein O is oxygen; C is carbon, and H is hydrogen;

R' is part of an alkyl phosphate triester groups, and said R' is selected from the group consisting of methyl, ethyl, isopropyl, propyl and higher alkyl homologs up to C-15;

X is selected from the group consisting of methyl, ethyl, propyl, and isopropyl and higher alkyl homologs to C-15;

R" is selected from the group consisting of OH, $OCH_3$, $OC_2H_5$, $OC_3H_7$, O-iso $C_3H_7$, $S^-$, and NR'''R'''' wherein N is nitrogen, R''' is a second alkyl radical selected from the group consisting of methyl, ethyl, propyl, isopropyl and alkyl homologs up to 16 carbons, and R'''' is a third alkyl radical selected from the group consisting of methyl, ethyl, propyl, isopropyl and alkyl homologs up to 16 carbons; and B, B', B" and B"" are natural and modified nucleobase radicals selected from the group consisting of 9-adeninyl, 1-thyminyl, 1-cytosinyl, 9-guaninyl, 9-hypoxanthinyl, 1-(5-methylcytosinyl), 1-(5-azacytosinyl), 1-(5-bromouracilyl), 1-(5-bromocytosinyl), 1-(5-fluorouracilyl), 1-(5-fluorocytosinyl), 1-(5-chlorouracilyl), 1-(5-chlorocytosinyl), 1-(5-iodouracilyl), 1-(5-iodocytosinyl), 1-(5-propynyluracilyl) and 1-(5-propynylcytosinyl).

7. A compound represented by the formula:

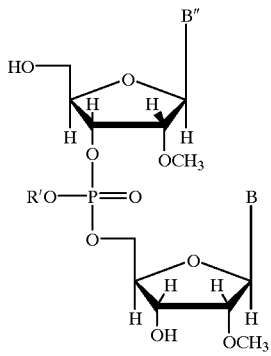

wherein O is oxygen; C is carbon, and H is hydrogen;

R' is part of an alkyl phosphate triester internucleosidyl group, and said R' is selected from the group consisting of methyl, ethyl, isopropyl, propyl and higher alkyl homologs to C-5; and B and B" are natural and modified nucleobase radicals selected from the group consisting of 9-adeninyl, 1-thyminyl, 1-cytosinyl, 9-guaninyl, 9-hypoxanthinyl, 1-(5-methylcytosinyl), 1-(5-azacytosinyl), 1-(5-bromouracilyl), 1-(5-bromocytosinyl), 1-(5-fluorouracilyl), 1-(5-fluorocytosinyl),1-(5-chlorocytosinyl), 1-(5-chlorouracilyl), 1-(5-iodouracilyl), 1-(5-iodocytosinyl), 1-(5-propynyluracilyl) and 1-(5-propynylcytosinyl).

8. A compound represented by the formula:

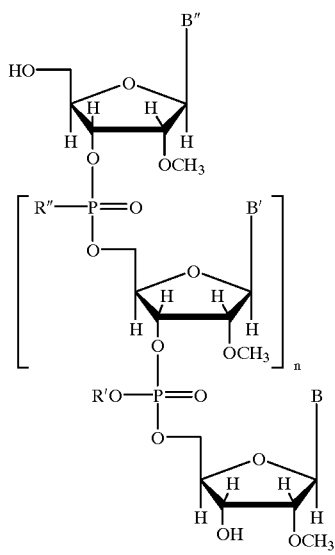

wherein n is 1–60;

O is oxygen; C is carbon, and H is hydrogen;

R' is part of an alkyl phosphate triesters located at the terminal 3' internucleosidyl position, and said R' is selected from the group of alkyl radicals consisting of methyl, ethyl, isopropyl, propyl and higher alkyl homologs up to C-5; and R" is selected from the group consisting of OH, $OCH_3$, $OC_2H_5$, and $S^-$;

B, B' and B" are natural and modified nucleobase radicals selected from the group consisting of 9-adeninyl, 1-thyminyl, 1-cytosinyl, 9-guaninyl, 9-hypoxanthinyl, 1-(5-methylcytosinyl), 1-(5-azacytosinyl), 1-(5-bromouracilyl), 1-(5-bromocytosinyl), 1-(5-fluorouracilyl), 1-(5-fluorocytosinyl), 1-(5-chlorocytosinyl), 1-(5-chlorouracilyl), 1-(5-iodouracilyl), 1-(5-iodocytosinyl), 1-(5-propynyluracilyl) and 1-(5-propynylcytosinyl).

9. A compound represented by the formula:

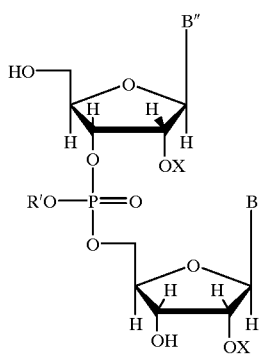

wherein O is oxygen; C is carbon, and H is hydrogen;

X is selected from the group consisting of ethyl, propyl, alkyl homologs up to 5 carbons and allyl;

R' is part of an alkyl phosphate triester group located at the internucleosidyl position, and said R' is an alkyl selected from the group consisting of methyl, ethyl, isopropyl, propyl and higher homologs up to C-5; and B and B" are natural and modified nucleobase radicals selected from the group consisting of 9-adeninyl, 1-thyminyl, 1-cytosinyl, 9-guaninyl, 9-hypoxanthinyl, 1-(5-methylcytosinyl), 1-(5-azacytosinyl), 1-(5-bromouracilyl), 1-(5-bronmocytosinyl), 1-(5-fluorouracilyl), 1-(5-fluorocytosinyl), 1-(5-chlorouracilyl), 1-(5-chlorocytosinyl), 1-(5-iodouracilyl), 1-(5-iodocytosinyl), 1-(5-propynyluracilyl) and 1-(5-propynylcytosinyl).

10. A compound represented by the formula:

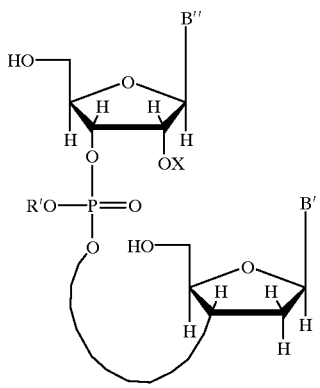

wherein O is oxygen; C is carbon, and H is hydrogen;

X is an alkyl group selected from the group consisting of methyl, ethyl, propyl, isopropyl and alkyl homologs up to C-5;

R' is part of an alkyl phosphate triesters located at the terminal 3' internucleosidyl position, and said R' is an alkyl selected from the group consisting of methyl, ethyl, isopropyl, propyl, and higher alkyl homologs up to C-5; and B and B" are natural and modified nucleobase radicals selected from the group consisting of 9-adeninyl, 1-thyminyl, 1-cytosinyl, 9-guaninyl, 9-hypoxanthinyl, 1-(5-methylcytosinyl), 1-(5-azacytosinyl), 1-(5-bromouracilyl), 1-(5-bromocytosinyl), 1-(5-fluorouracilyl), 1-(5-fluorocytosinyl), 1-(5-chlorouracilyl), 1-(5-chlorocytosinyl), 1-(5-iodouracilyl), 1-(5-iodocytosinyl), 1-(5-propynyluracilyl) and 1-(5-propynylcytosinyl).

11. A compound represented by the formula:

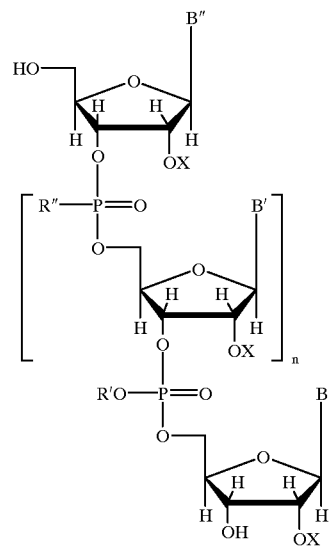

wherein n is 1–60;

O is oxygen; C is carbon, and H is hydrogen;

R' is part of an alkyl phosphate triester group located at the terminal 3' internucleosidyl position, and said R' is an alkyl group selected from the group consisting of methyl, ethyl, isopropyl, propyl and higher alkyl homologs up to C-5;

R" is selected from the group consisting of OH, $OCH_3$, $OC_2H_5$, $OC_3H_7$, O-iso $C_3H_7$, and $S^-$, X is selected from the group consisting of methyl, ethyl, propyl, isopropyl and higher alkyl homologs to C-5; and B, B' and B" are natural and modified nucleobase radicals selected from the group consisting of 9-adeninyl, 1-thyminyl, 1-cytosinyl, 9-guaninyl, 9-hypoxanthinyl, 1-(5-methylcytosinyl), 1-(5-azacytosinyl), 1-(5-bromouracilyl), 1-(5-bromocytosinyl), 1-(5-fluorouracilyl), 1-(5-fluorocytosinyl), 1-(5-chlorouracilyl), 1-(5-chlorocytosinyl), 1-(5-iodouracilyl), 1-(5-iodocytosinyl), 1-(5-propynyluracilyl) and 1-(5-propynylcytosinyl).

12. A compound represented by the formula:

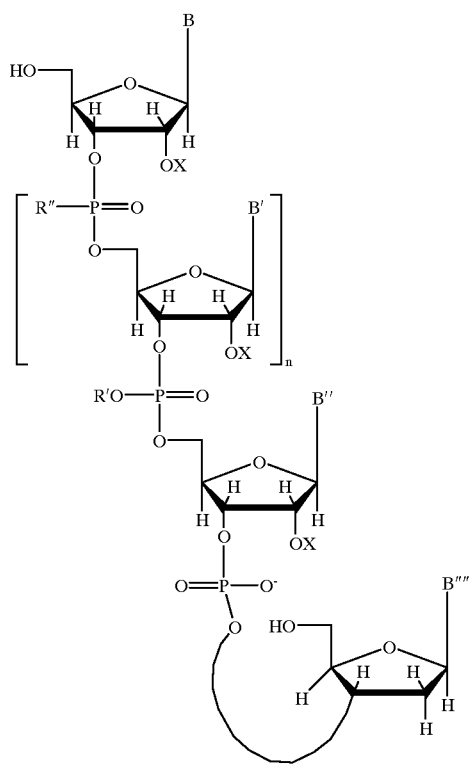

wherein n is 1–60;

wherein O is oxygen; C is carbon, and H is hydrogen;

R' is part of an alkyl phosphate triester groups, and said R' is selected from the group consisting of methyl, ethyl, isopropyl, propyl and higher alkyl homologs up to C-5;

X is selected from the group consisting of methyl, ethyl, propyl, and isopropyl and higher alkyl homologs to C-5;

R" is selected from the group consisting of OH, $OCH_3$, $OC_2H_5$, $OC_3H_7$, O-iso $C_3H_7$, and $S^-$; and B, B', B" and B"" are natural and modified nucleobase radicals selected from the group consisting of 9-adeninyl, 1-thyminyl, 1-cytosinyl, 9-guaninyl, 9-hypoxanthinyl, 1-(5-methylcytosinyl), 1-(5-azacytosinyl), 1-(5-bromouracilyl), 1-(5-bromocytosinyl), 1-(5-fluorouracilyl), 1-(5-fluorocytosinyl), 1-(5-chlorouracilyl), 1-(5-chlorocytosinyl), 1-(5-iodouracilyl), 1-(5-iodocytosinyl), 1-(5-propynyluracilyl) and 1-(5-propynylcytosinyl).

13. A composition comprising an oligonucleotide sequence and an acceptable carrier, wherein said oligonucleotide sequence contains one of the oligonucleotide structures of any of claims 1–12.

14. The composition of claim 13 wherein said pharmaceutically acceptable carrier is a lipofectin.

\* \* \* \* \*